(12) United States Patent
Dave et al.

(10) Patent No.: US 10,457,748 B2
(45) Date of Patent: Oct. 29, 2019

(54) SINGLE LINKER FABFV ANTIBODIES AND METHODS OF PRODUCING SAME

(71) Applicant: UCB Biopharma SPRL, Brussels (BE)

(72) Inventors: Emma Dave, Slough (GB); Sam Philip Heywood, Slough (GB); David Paul Humphreys, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 14/654,240

(22) PCT Filed: Dec. 20, 2013

(86) PCT No.: PCT/EP2013/077758
§ 371 (c)(1),
(2) Date: Jun. 19, 2015

(87) PCT Pub. No.: WO2014/096390
PCT Pub. Date: Jun. 26, 2014

(65) Prior Publication Data
US 2016/0017057 A1    Jan. 21, 2016

(30) Foreign Application Priority Data
Dec. 21, 2012  (GB) .................... 1223276.5

(51) Int. Cl.
C07K 16/18        (2006.01)
C07K 16/46        (2006.01)
C07K 16/28        (2006.01)

(52) U.S. Cl.
CPC ............ *C07K 16/468* (2013.01); *C07K 16/18* (2013.01); *C07K 16/2878* (2013.01); *C07K 2317/55* (2013.01); *C07K 2317/56* (2013.01); *C07K 2317/624* (2013.01); *C07K 2317/64* (2013.01); *C07K 2317/92* (2013.01); *C07K 2319/00* (2013.01)

(58) Field of Classification Search
CPC .. C07K 16/18; C07K 16/468; C07K 2317/55; C07K 2317/64; C07K 2317/56
USPC ........... 424/136.1; 435/252.3, 252.31, 320.1, 435/328, 69.6; 530/387.3; 536/23.4
See application file for complete search history.

(56) References Cited

U.S. PATENT DOCUMENTS

| | | | |
|---|---|---|---|
| 4,741,900 A | 5/1988 | Alvarez et al. | |
| 5,219,996 A | 6/1993 | Bodmer et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,454,806 A | 10/1995 | Shinonome | |
| 5,516,637 A | 5/1996 | Huang et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,667,425 A | 9/1997 | Pineau et al. | |
| 5,685,727 A | 11/1997 | Cairns | |
| 5,698,426 A | 12/1997 | Huse | |
| 5,733,743 A | 3/1998 | Johnson et al. | |

(Continued)

FOREIGN PATENT DOCUMENTS

| EP | 0 392 745 B1 | 10/1990 |
|---|---|---|
| EP | 0 438 474 B1 | 7/1991 |

(Continued)

OTHER PUBLICATIONS

Dave et al. MAbs. Oct. 2016; 8(7): 1319-1335.*
Metz et al. (Protein Engineering, Design & Selection vol. 25 No. 10 pp. 571-580, 2012 Published online Sep. 13, 2012).*
Cole et al., "Monoclonal Antibodies and Cancer Therapy", Journal of Cellular Biochemistry, 1985, 42 pages.
Glockshuber et al., "A Comparison of Strategies to Stabilize Immunoglobulin Fv-Fragments", Biochemistry, 1990, 29(6), 1362-1367.
Köhler et al., "Pillars Article: Continuous cultures of fused cells secreting antibody of predefined specificity", Nature, 1975, 256(2217) 495-497.

(Continued)

*Primary Examiner* — Lynn A Bristol
(74) *Attorney, Agent, or Firm* — McDonnell Boehnen Hulbert & Berghoff LLP

(57) ABSTRACT

The present disclosure relates to a multi-specific antibody molecule comprising or consisting of three polypeptides: a) a polypeptide chain of formula (I): $(Vxx)_n Vx\text{-}Cx\text{-}X\text{-}V_1$; and b) a polypeptide chain of formula (II): $(Vyy)_n Vy\text{-}Cy$ c) a polypeptide of formula (III): $V_2$ wherein Vx represents a variable domain, Vxx represents a variable domain, Cx represents a constant region, X represents a linker, V represents a variable domain, Vy represents a variable domain, Vyy represents a variable domain, Cy represents a constant region, $V_2$ represents a variable domain, $_n$ independently represents 0 or 1, wherein the polypeptide chain of formula (I) and the polypeptide chain of formula (II) is aligned such that the constant regions Cx and Cy are paired and the variable domains Vx and Vy are paired to form a binding domain and optionally a disulphide bond is present between V and $V_2$, in particular where a disulphide bond is present. The disclosure also extends to pharmaceutical formulation comprising the construct, DNA encoding the constructs and vectors comprising same. The disclosure further extends to a method of expressing the constructs, for example in a host cell and methods for formulating same as a pharmaceutical composition. The disclosure also relates to use of the constructs and formulations in treatment.

24 Claims, 10 Drawing Sheets
Specification includes a Sequence Listing.

(56) References Cited

U.S. PATENT DOCUMENTS

| | | | |
|---|---|---|---|
| 5,750,753 A | 5/1998 | Kimae et al. | |
| 5,770,429 A | 6/1998 | Lonberg et al. | |
| 5,780,225 A | 7/1998 | Wigler et al. | |
| 5,821,047 A | 10/1998 | Garrard et al. | |
| 5,969,108 A | 10/1999 | McCafferty et al. | |
| 2012/0283415 A1* | 11/2012 | Humphreys | C07K 7/06 530/387.3 |
| 2012/0316324 A1* | 12/2012 | Adams | C07K 16/18 530/387.3 |
| 2013/0066054 A1* | 3/2013 | Humphreys | A61K 47/48215 530/391.1 |
| 2013/0243772 A1* | 9/2013 | Adams | C07K 16/2866 424/136.1 |
| 2014/0141468 A1* | 5/2014 | Ellis | C07K 16/2875 435/69.6 |
| 2014/0302033 A1* | 10/2014 | Adams | C07K 16/18 424/135.1 |
| 2016/0333105 A1* | 11/2016 | Adams | C07K 16/2878 |

FOREIGN PATENT DOCUMENTS

| | | |
|---|---|---|
| EP | 0 463 151 B1 | 1/1992 |
| EP | 0 546 073 B1 | 6/1993 |
| EP | 0 948 544 B1 | 10/1999 |
| EP | 1 090 037 B1 | 4/2001 |
| WO | 86/01533 A1 | 3/1986 |
| WO | 89/00195 A1 | 1/1989 |
| WO | 89/01476 A1 | 2/1989 |
| WO | 00/02809 A1 | 3/1990 |
| WO | 91/09967 A1 | 7/1991 |
| WO | 91/10737 A1 | 7/1991 |
| WO | 92/01047 A1 | 1/1992 |
| WO | 92/02551 A1 | 2/1992 |
| WO | 92/18619 A1 | 10/1992 |
| WO | 92/22583 A1 | 12/1992 |
| WO | 93/06231 A1 | 4/1993 |
| WO | 93/11236 A1 | 6/1993 |
| WO | 95/15982 A1 | 6/1995 |
| WO | 95/20401 A1 | 8/1995 |
| WO | 08/20734 A1 | 5/1998 |
| WO | 98/25971 A1 | 6/1998 |
| WO | 98/55607 A2 | 12/1998 |
| WO | 99/37791 A1 | 7/1999 |
| WO | 03/031581 A2 | 4/2003 |
| WO | 2004/051268 A1 | 6/2004 |
| WO | 2004/106377 A1 | 12/2004 |
| WO | 2005/003170 A2 | 1/2005 |
| WO | 2005/117984 A2 | 12/2005 |
| WO | 2007/106120 A2 | 9/2007 |
| WO | 2008/038024 A1 | 4/2008 |
| WO | 2009/018386 A1 | 2/2009 |
| WO | 2009021754 A2 | 2/2009 |
| WO | 2009/040562 A1 | 4/2009 |
| WO | 2010/035012 A1 | 4/2010 |
| WO | 2010115552 A1 | 10/2010 |
| WO | 2010115589 A1 | 10/2010 |
| WO | 2011/030107 A1 | 3/2011 |
| WO | 2011/030305 A2 | 3/2011 |
| WO | 2011/036460 A1 | 3/2011 |
| WO | 2012/025525 A1 | 3/2012 |
| WO | 2012025525 A1 | 3/2012 |

OTHER PUBLICATIONS

Lanaro et al., "Red Blood Cell Survival in Patients with Hodgkin's Disease", Cancer, 1971, 28(3), 658-661.

Luo et al., "V1-Linker-Vh Orientation-Dependent Expression of Single Chain Fv Containing an Engineered Disulfide-Stabilized Bond in the Framework Regions", J. Biochem., 1995, vol. 118, 825-831.

Persic et al., "An integrated vector system for the eukaryotic expression of antibodies or their fragments after selection from phage display libraries", Gene, 1997, vol. 187, 9-18.

Zalipsky et al., "Introduction to Chemistry and Biological Applications of Poly (ethylene glycol", ACS Symposium Series, American Chemical Society, 1997, 13 pages.

Rajagopal et al., "A form of anti-Tac(Fv) which is both single-chain and disulfide stabilized: comparison with its single-chain and disulfide-stabilized homologs", Protein Engineering, 1997, 10(12), 1453-1459.

Riechmann et al., "Reshaping human antibodies for therapy", Nature, 1988, vol. 332, 323-327.

Reiter et al., "Improved Binding and Antitumor Activity of a Recombinant Anti-erbB2 Immunotoxin by Disulfide Stabilization of the Fv Fragmen", The Journal of Biological Chemistry, 1994, 269(28), 18327-18331.

Wells et al., "Cassette mutagenesis: an efficient method for generation of multiple mutations at defined sites", Gene, 1985, vol. 34, 315-323.

Yang et al., "CDR Walking Mutagenesis for the Affinity Maturation of a Potent Human Anti-HIV-1 Antibody into the Picomolar Range", J. Mol. Biol., 1995, vol. 254, 392-403.

Young et al., "Thermal stabilization of a single-chain Fv antibody fragment by introduction of a disulphide bond", FEBS Letters, 1995, vol. 377, 135-139.

Zhang et al., "PowerBLAST: A New Network BLAST Application for Interactive or Automated Sequence Analysis and Annotation", Genome Research, 1997, vol. 7, 649-656.

Zhu et al., "Remodeling domain interfaces to enhance heterodimer formation", Protein Science, 1997, vol. 6, 781-788.

Reiter et al., "Engineering antibody Fv fragments for cancer detection and therapy: Disulfide-stabilized Fv fragments", Nature Biotechnology, 1996, vol. 14, 1239-1245.

Jung et al., "Design of Interchain Disulfide Bonds in the Framework Region of the Fv Fragment of the Monoclonal Antibody B3", Proteins: Structure, Function, and Genetics, 1994, vol. 19, 35-47.

Brikmann et al., "Phage display of disulfide-stabilized Fv fragments", Journal of Immunological Methods, 1995, vol. 182, 41-50.

Ames et al., "Conversion of murine Fabs isolated from a combinatorial phage display library to full length immunoglobulins", Journal of Immunological Methods, 1995, vol. 184, 177-186.

Kettleborough et al, "Isolation of tumor cell-specific single-chain Fv from immunized mice using phage-antibody libraries and the re-construction of whole antibodies from these antibody fragments", Eur. J. Immunol., 1994, vol. 24, 952-958.

Burton et al., "Human Antibodies from Combinatorial Libraries", Advances in Immunology, 1994, vol. 57, 191-280.

Vaughan et al., "Human antibodies by design", Nature Biotechnology, 1998, vol. 16, 535-539.

Kashmiri et al., "SDR grafting—a new approach to antibody humanization", Methods, 2005, vol. 36, 25-34.

Gish et al., "Identification of protein coding regions by database similarity search", Nature Genetics, 1993, vol. 3, 266-272.

Madden et al., "[9] Application of Network BLAST Server", Methods in Enzymology, 1996, vol. 266, 131-141.

Marks et al., "By-Passing Immunization: Building High Affinity Human Antibodies by Chain Shuffling", Bio/Technology, 1992, vol. 10, 779-783.

Patten et al., "Applications of DNA shuffling to pharmaceuticals and vaccines", Curr. Opin. Biotechnol, 1997, vol. 8, 724-733.

Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity", J. Mol. Biol., 1996, vol. 256, 77-88.

Crameri et al., "DNA shuffling of a family of genes from diverse species accelerates directed evolution", Nature, 1998, vol. 391, 288-291.

Thorpe et al., "The Preparation and Cytotoxic Properties of Antibody-Toxin Conjugates", Immunological Rev., 1982, vol. 62, 119-158.

Dubowchik et al., "Receptor-mediated and enzyme-dependent targeting of cytotoxic anticancer drugs", Pharmacology & Therapeutics, 1999, vol. 83, 67-123.

Chapman, "PEGylated antibodies and antibody fragments for improved therapy: a review", Advanced Drug Delivery Reviews, 2002, vol. 54, 531-545.

(56) References Cited

OTHER PUBLICATIONS

Harris, "Introduction to Biotechnical and Biomedical Applications of Poly(Ethylene Glycol)", Springer Science+Business Media, New York, 1992, 5 pages.

Altschul et al., "Basic Local Alignment Search Tool", J. Mol. Biol., 1990, vol. 215, 403-410.

Altschul et al., "Gapped BLAST and PSI-BLAST: a new generation of protein database search programs", Nucleic Acids Research, 1997, 25(17), 3389-3402.

Ausubel et al., "Current Protocols in Molecular Biology", Greene Publishing & Wiley Interscience, New York, 1993, 4,648 pages.

Babcook et al., "A novel strategy for generating monoclonal antibodies from single, isolated lymphocytes producing antibodies of defined specificities", Proc. Natl. Acad. Sci. USA, Immunology, 1996, 93(15), 7843-7848.

Brinkmann et al., "A recombinant immunotoxin containing a disulfide-stabilized Fv fragment", Proc. Natl. Acad. Sci. USA, Immunology, 1993, vol. 90, 7538-7542.

Schoonjans et al., "A new model for intermediate molecular weight recombinant bispecific and trispecific antibodies by efficient heterodimerization of single chain variable domains through fusion to a Fab-chain", Biomolecular Engineering, 2001, vol. 17, 193-202.

Schoonjans et al., "Fab Chains as an Efficient Heterodimerization Scaffold for the Production of Recombinant Bispecific and Trispecific Antibody Derivatives", The Journal of Immunology, 2000, 7050-7057.

Lu et al., "Fab-scFv fusion protein: an efficient approach to production of bispecific antibody fragments", Journal of Immunological Methods, 2002, vol. 267, 213-226.

Metz et al., "Bispecific antibody derivatives with restricted binding functionalities that are activated by proteolytic processing", Protein Engineering, Design & Selection, 2012, 25(10), 571-580.

Miller et al., "Design, Construction, and in Vitro Analyses of Multivalent Antibodies", The Journal of Immunology, 2003, vol. 170, 4854-4861.

* cited by examiner

Figure 1A A26Fab-645dsFv

A26 Fab Heavy-(S, 3xG4S/T)-645dsvH      (SEQ ID NO: 1)

EVQLVESGGG LVQPGGSLRL SCAASGFTFT NYGIHWIRQA PGKGLEWVAS ISPSGGLTYY
RDSVKGRFTI SRDDAKNSPY LQMNSLRAED TAVYYCATGG EGIFDYWGQG TLVTVSSAST
KGPSVFPLAP SSKSTSGGTA ALGCLVKDYF PEPVTVSWNS GALTSGVHTF PAVLQSSGLY
SLSSVVTVPS SSLGTQTYIC NVNHKPSNTK VDKKVEPKSC SGGGGSGGGG TGGGGSEVQL
LESGGGLVQP GGSLRLSCAV SGIDLSNYAI NWVRQAPGKC LEWIGIIWAS GTTFYATWAK
GRFTISRDNS KNTVYLQMNS LRAEDTAVYY CARTVPGYST APYFDLWGQG
TLVTVSS

A26 Fab Light-(S, 3xG4S)-645dsvL       (SEQ ID NO: 2)

DIQMTQSPSS LSASVGDRVT ITCRATQSIY NALAWYQQKP GKAPKLLIYN ANTLHTGVPS
RFSASGSGTD STLTISSLQP EDFATYYCQQ YYDYPLTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGECSGGGGS GGGGSGGGGS DIQMTQSPSS
VSASVGDRVT ITCQSSPSVW SNFLSWYQQK PGKAPKLLIY EASKLTSGVP SRFSGSGSGT
DFTLTISSLQ PEDFATYYCG GYSSISDTT FGCGTKVEIK RT

Figure 1B Single linker A26Fab-645dsFv (LC-vL linked)

A26 Fab Heavy                (SEQ ID NO: 3)

EVQLVESGGG LVQPGGSLRL SCAASGFTFT NYGIHWIRQA PGKGLEWVAS ISPSGGLTYY
RDSVKGRFTI SRDDAKNSPY LQMNSLRAED TAVYYCATGG EGIFDYWGQG TLVTVSSAST
KGPSVFPLAP SSKSTSGGTA ALGCLVKDYF PEPVTVSWNS GALTSGVHTF PAVLQSSGLY
SLSSVVTVPS SSLGTQTYIC NVNHKPSNTK VDKKVEPKSC

645dsvH           (SEQ ID NO: 4)

EVQLLESGGG LVQPGGSLRL SCAVSGIDLS NYAINWVRQA PGKCLEWIGI IWASGTTFYA
TWAKGRFTIS RDNSKNTVYL QMNSLRAEDT AVYYCARTVP GYSTAPYFDL WGQGTLVTVSS

A26 Fab Light-(S, 3xG4S)-645dsvL       (SEQ ID NO: 5)

DIQMTQSPSS LSASVGDRVT ITCRATQSIY NALAWYQQKP GKAPKLLIYN ANTLHTGVPS
RFSASGSGTD STLTISSLQP EDFATYYCQQ YYDYPLTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGECSGGGGS GGGGSGGGGS DIQMTQSPSS
VSASVGDRVT ITCQSSPSVW SNFLSWYQQK PGKAPKLLIY EASKLTSGVP SRFSGSGSGT
DFTLTISSLQ PEDFATYYCG GYSSISDTT FGCGTKVEIK RT

Figure 1C Single linker A26Fab-645dsFv (HC-vH linked)

A26 Fab Heavy-(S, 3xG4S/T)-645dsvH         (SEQ ID NO: 6)

```
EVQLVESGGG LVQPGGSLRL SCAASGFTFT NYGIHWIRQA PGKGLEWVAS ISPSGGLTYY
RDSVKGRFTI SRDDAKNSPY LQMNSLRAED TAVYYCATGG EGIFDYWGQG TLVTVSSAST
KGPSVFPLAP SSKSTSGGTA ALGCLVKDYF PEPVTVSWNS GALTSGVHTF PAVLQSSGLY
SLSSVVTVPS SSLGTQTYIC NVNHKPSNTK VDKKVEPKSC SGGGGSGGGG TGGGGSEVQL
LESGGGLVQP GGSLRLSCAV SGIDLSNYAI NWVRQAPGKC LEWIGIIWAS GTTFYATWAK
GRFTISRDNS KNTVYLQMNS LRAEDTAVYY CARTVPGYST APYFDLWGQG TLVTVSS
```

A26 Fab Light         (SEQ ID NO: 7)

```
DIQMTQSPSS LSASVGDRVT ITCRATQSIY NALAWYQQKP GKAPKLLIYN ANTLHTGVPS
RFSASGSGTD STLTISSLQP EDFATYYCQQ YYDYPLTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC
```

645dsvL         (SEQ ID NO: 8)

```
DIQMTQSPSS VSASVGDRVT ITCQSSPSVW SNFLSWYQQK PGKAPKLLIY EASKLTSGVP
SRFSGSGSGT DFTLTISSLQ PEDFATYYCG GGYSSISDTT FGCGTKVEIK RT
```

Figure 1D A26Fab-645dsscFv (HC-scFv)

A26 Fab Heavy-(S, 2xG4S/T)-645dsscFv(vH-4xG4S-vL)     (SEQ ID NO: 9)

```
EVQLVESGGG LVQPGGSLRL SCAASGFTFT NYGIHWIRQA PGKGLEWVAS ISPSGGLTYY
RDSVKGRFTI SRDDAKNSPY LQMNSLRAED TAVYYCATGG EGIFDYWGQG TLVTVSSAST
KGPSVFPLAP SSKSTSGGTA ALGCLVKDYF PEPVTVSWNS GALTSGVHTF PAVLQSSGLY
SLSSVVTVPS SSLGTQTYIC NVNHKPSNTK VDKKVEPKSC SGGGGTGGGG SEVQLLESGG
GLVQPGGSLR LSCAVSGIDL SNYAINWVRQ APGKCLEWIG IIWASGTTFY ATWAKGRFTI
SRDNSKNTVY LQMNSLRAED TAVYYCARTV PGYSTAPYFD LWGQGTLVTV SSGGGGSGGG
GSGGGGSGGG GSDIQMTQSP SSVSASVGDR VTITCQSSPS VWSNFLSWYQ QKPGKAPKLL
IYEASKLTSG VPSRFSGSGS GTDFTLTISS LQPEDFATYY CGGGYSSISD TTFGCGTKVE
IKRT
```

A26 Fab Light         (SEQ ID NO: 10)

```
DIQMTQSPSS LSASVGDRVT ITCRATQSIY NALAWYQQKP GKAPKLLIYN ANTLHTGVPS
RFSASGSGTD STLTISSLQP EDFATYYCQQ YYDYPLTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC
```

Figure 1E A26Fab-645dsscFv (LC-scFv)

A26 Fab Heavy                               (SEQ ID NO: 11)
EVQLVESGGGLVQPGGSLRLSCAASGFTFTNYGIHWIRQAPGKGLEWVASISPSGGLTYYRDSVKGRFTISR
DDAKNSPYLQMNSLRAEDTAVYYCATGGEGIFDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVE
PKSC A26 Fab Light-(S, 2xG4S)-645dsscFv(vH-4xG4S-vL)   (SEQ ID NO: 12)
DIQMTQSPSSLSASVGDRVTITCRATQSIYNALAWYQQKPGKAPKLLIYNANTLHTGVPSRFSASGSGTDST
LTISSLQPEDFATYYCQQYYDYPLTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGECSG
GGGSGGGGSEVQLLESGGGLVQPGGSLRLSCAVSGIDLSNYAINWVRQAPGKCLEWIGIIWASGTTFYATWA
KGRFTISRDNSKNTVYLQMNSLRAEDTAVYYCARTVPGYSTAPYFDLWGQGTLVTVSSGGGGSGGGGSGGGG
SGGGGSDIQMTQSPSSVSASVGDRVTITCQSSPSVWSNFLSWYQQKPGKAPKLLIYEASKLTSGVPSRFSGS
GSGTDFTLTISSLQPEDFATYYCGGGYSSISDTTFGCGTKVEIKRT

Figure 1F

Fab LC                          (SEQ ID NO: 81)
DIQMTQSPSSLSASVGDRVTITCRATQSIYNALAWYQQKPGKAPKLLIYNANTLHTGVPSRFSASGSGTDST
LTISSLQPEDFATYYCQQYYDYPLTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

Fab-648gH1 HC                   (SEQ ID NO: 82)
EVQLVESGGGLVQPGGSLRLSCAASGFTFTNYGIHWIRQAPGKGLEWVASISPSGGLTYYRDSVKGRFTISR
DDAKNSPYLQMNSLRAEDTAVYYCATGGEGIFDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVE
PKSCSGGGGSGGGGTGGGGSEVQLVESGGGLVQPGGSLRLSCAVSGFSLSRYAMTWVRQAPGKCLEWIGTIT
TGGNTNYANWAKGRFTISKDSTTVYLQMNSLRAEDTAVYYCARGGYVSYADATELSLWGQGTLVTVSS

648gL1                          (SEQ ID NO: 83)
DIVMTQSPSTLSASVGDRVTITCQASQSIGSRLAWYQQKPGKAPKLLIYYASTVASGVPSRFKGSGSGTEFT
LTISSLQPDDFATYYCQSYDYSSSSSYAFGCGTKVEIKRT

Fab HC                          (SEQ ID NO: 84)
EVQLVESGGGLVQPGGSLRLSCAASGFTFTNYGIHWIRQAPGKGLEWVASISPSGGLTYYRDSVKGRFTISR
DDAKNSPYLQMNSLRAEDTAVYYCATGGEGIFDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVE
PKSC

Fab-648gL1 LC                   (SEQ ID NO: 85)
DIQMTQSPSSLSASVGDRVTITCRATQSIYNALAWYQQKPGKAPKLLIYNANTLHTGVPSRFSASGSGTDST
LTISSLQPEDFATYYCQQYYDYPLTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGECSG
GGGSGGGGSGGGGSDIVMTQSPSTLSASVGDRVTITCQASQSIGSRLAWYQQKPGKAPKLLIYYASTVASGV
PSRFKGSGSGTEFTLTISSLQPDDFATYYCQSYDYSSSSSYAFGCGTKVEIKRT

648gH1                          (SEQ ID NO: 86)
EVQLVESGGGLVQPGGSLRLSCAVSGFSLSRYAMTWVRQAPGKCLEWIGTITTGGNTNYANWAKGRFTISKD
STTVYLQMNSLRAEDTAVYYCARGGYVSYADATELSLWGQGTLVTVSS

CDRH1: GIDLSNYAIN (SEQ ID NO:87)

CDRH2: IIWASGTTFYATWAKG (SEQ ID NO:88)

CDRH3: TVPGYSTAPYFDL (SEQ ID NO:89)

645L

CDRL1: QSSPSVWSNFLS (SEQ ID NO:90)

CDRL2: EASKLTS (SEQ ID NO:91)

CDRL3: GGGYSSISDTT (SEQ ID NO:92)

648H

CDRH1: GFSLSRYAMT (SEQ ID NO:93)

CDRH2: TITTGGNTNYANWAKG (SEQ ID NO:94)

CDRH3: GGYVSYADATELSL (SEQ ID NO:95)

648L

CDRL1: QASQSIGSRLA (SEQ ID NO:96)

CDRL2: YASTVAS (SEQ ID NO:97)

CDRL3: QSYDYSSSSYA (SEQ ID NO:98)

(a) Heavy chain variable domain of anti-albumin antibody (no ds) (SEQ ID NO:99)

EVQLLESGGGLVQPGGSLRLSCAVSGIDLSNYAINWVRQAPGKGLEWIGIIWASGTTFYATWAKGRFTISRDNSKNTVYL
QMNSLRAEDTAVYYCARTVPGYSTAPYFDLWGQGTLVTVSS

(b) Heavy chain variable domain of anti-albumin antibody (ds) (SEQ ID NO:100)

EVQLLESGGGLVQPGGSLRLSCAVSGIDLSNYAINWVRQAPGKCLEWIGIIWASGTTFYATWAKGRFTISRDNSKNTVYL
QMNSLRAEDTAVYYCARTVPGYSTAPYFDLWGQGTLVTVSS

(c) Light chain variable domain of anti-albumin antibody (no ds) (SEQ ID NO:101)

DIQMTQSPSSVSASVGDRVTITCQSSPSVWSNFLSWYQQKPGKAPKLLIYEASKLTSGVPSRFSGSGSGTDFTLTISSLQ
PEDFATYYCGGGYSSISDTTFGGGTKVEIKRT

(d) Light chain variable domain of anti-albumin antibody (ds) (SEQ ID NO:102)

DIQMTQSPSSVSASVGDRVTITCQSSPSVWSNFLSWYQQKPGKAPKLLIYEASKLTSGVPSRFSGSGSGTDFTLTISSLQ
PEDFATYYCGGGYSSISDTTFGCGTKVEIKRT

Figure 2

Reducing SDS-PAGE of Protein-G purified A26Fab-645dsFv, A26Fab-645dsscFv and single linker A26Fab-645dsFv expressed by HEK293 cells

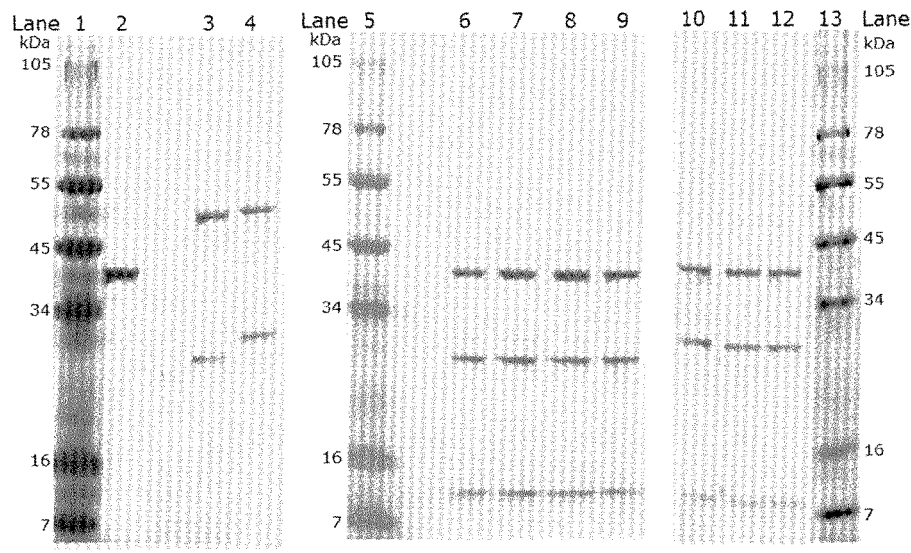

| Lane | Sample |
|---|---|
| 1 | Seeblue Plus 2 molecular weight markers |
| 2 | A26Fab-645dsFv |
| 3 | A26Fab-645dsscFv (LC-scFv) |
| 4 | A26Fab-645dsscFv (HC-scFv) |
| 5 | Seeblue Plus 2 molecular weight markers |
| 6 | single linker A26Fab-645dsFv (LC-vL linked) (ratio 1:1:1 LC-vL:HC:vH) |
| 7 | single linker A26Fab-645dsFv (LC-vL linked) (ratio 1:1:2 LC-vL:HC:vH) |
| 8 | single linker A26Fab-645dsFv (LC-vL linked) (ratio 2:1:2 LC-vL:HC:vH) |
| 9 | single linker A26Fab-645dsFv (LC-vL linked) (ratio 1:2:2 LC-vL:HC:vH) |
| 10 | single linker A26Fab-645dsFv (HC-vH linked) (ratio 1:1:1 HC-vH:LC:vL) |
| 11 | single linker A26Fab-645dsFv (HC-vH linked) (ratio 1:1:2 HC-vH:LC:vL) |
| 12 | single linker A26Fab-645dsFv (HC-vH linked) (ratio 2:1:2 HC-vH:LC:vL) |
| 13 | Seeblue Plus 2 molecular weight markers |

G3000 SEC-HPLC analysis of Protein-G purified A26Fab-645dsFv, A26Fab-645dsscFv and single linker A26Fab-645dsFv expressed by HEK293 cells

$V_1$ and $V_2$   Light chain variable domain ⬭ or heavy chain variable domain ⬭

Linker (X) ■

— Disulfide bond

Variable region of light chain (VL) ☐

Variable region of heavy chain (VH) ☐

Constant region cKappa ($C_L$) ☐

Constant region ($CH_1$) ☐

Figure 5 Transient expression of single linker A26Fab-dsFvs expressed from triple gene plasmids in CHO cells.
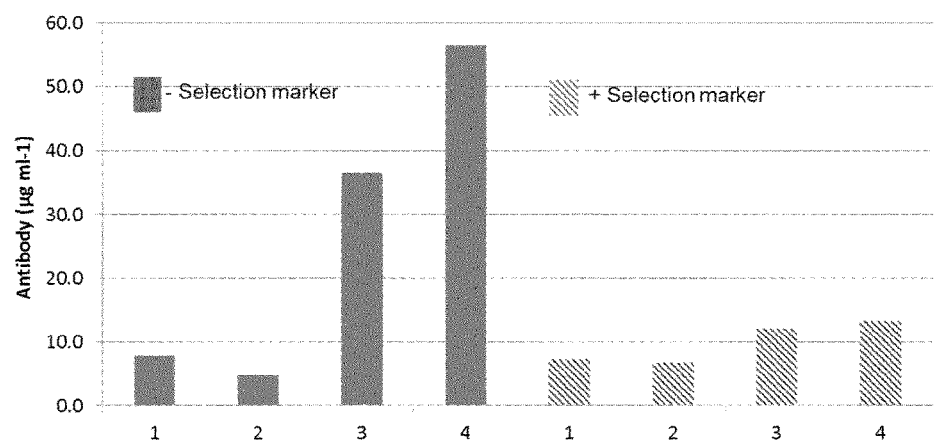
| Column | Sample |
|---|---|
| 1 | Single linker A26Fab-645dsFv (HC-vH linked) |
| 2 | Single linker A26Fab-648dsFv (HC-vH linked) |
| 3 | Single linker A26Fab-645dsFv (LC-vL linked) |
| 4 | Single linker A26Fab-648dsFv (LC-vL linked) |

Figure 6 Reducing SDS-PAGE of Protein-G purified Single linker A26Fab-645dsFvs and A26Fab-648dsFvs expressed from Triple Gene Plasmids in CHO cells.

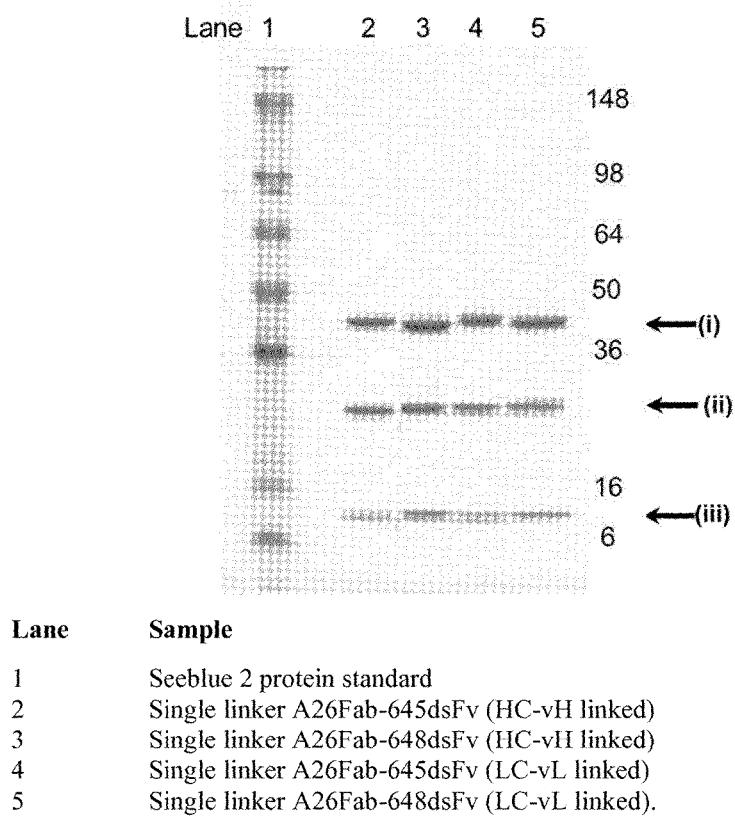

| Lane | Sample |
|---|---|
| 1 | Seeblue 2 protein standard |
| 2 | Single linker A26Fab-645dsFv (HC-vH linked) |
| 3 | Single linker A26Fab-648dsFv (HC-vH linked) |
| 4 | Single linker A26Fab-645dsFv (LC-vL linked) |
| 5 | Single linker A26Fab-648dsFv (LC-vL linked). | where (i) A26Fab light heavy linked to 645vL or 648vL ($M_r$, ~36 kDa) or A26Fab light heavy linked to 645vH or 648vH ($M_r$, ~37 kDa); (ii) A26Fab light ($M_r$, ~24 kDa) or A26Fab heavy ($M_r$, ~24 kDa); (iii) 645vL, 648vL, 645vH or 648vH ($M_r$, ~12-13 kDa).

Figure 7 G3000 SEC-HPLC analysis of Protein-G purified single linker A26Fab-645dsFvs and single linker A26Fab-648dsFvs expressed from triple gene plasmids in CHO cells
Single linker A26Fab-645dsFv (HC-vH linked)
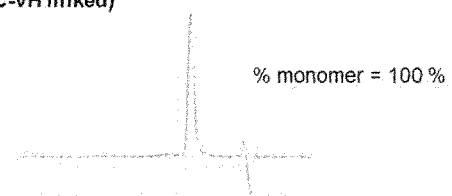
% monomer = 100 %
Single linker A26Fab-648dsFv (HC-vH linked)
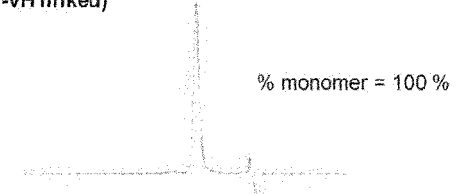
% monomer = 100 %
Single linker A26Fab-645dsFv (LC-vL linked)
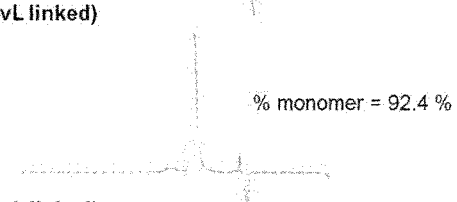
% monomer = 92.4 %
Single linker A26Fab-648dsFv (LC-vL linked)
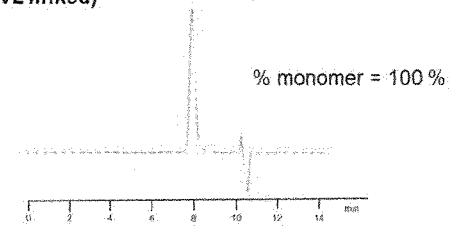
% monomer = 100 %

SEQUENCE LISTING

```
<160> NUMBER OF SEQ ID NOS: 104

<210> SEQ ID NO 1
<211> LENGTH: 357
<212> TYPE: PRT
<213> ORGANISM: Artificial Sequence
<220> FEATURE:
<223> OTHER INFORMATION: A26 Fab Heavy-(S, 3xG4S/T)-645dsvH

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95
```

```
Ala Thr Gly Gly Glu Gly Ile Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Thr Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

Gly Tyr Ser Thr Ala Pro Tyr Phe Asp Leu Trp Gly Gln Gly Thr Leu
            340                 345                 350

Val Thr Val Ser Ser
        355

<210> SEQ ID NO 2
<211> LENGTH: 342
<212> TYPE: PRT
<213> ORGANISM: Artificial Sequence
<220> FEATURE:
<223> OTHER INFORMATION: A26 Fab Light-(S, 3xG4S)-645dsvL

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95
```

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys Ser Gly Gly Gly Ser Gly Gly Gly Gly
            210                 215                 220

Ser Gly Gly Gly Gly Ser Asp Ile Gln Met Thr Gln Ser Pro Ser Ser
225                 230                 235                 240

Val Ser Ala Ser Val Gly Asp Arg Val Thr Ile Thr Cys Gln Ser Ser
                245                 250                 255

Pro Ser Val Trp Ser Asn Phe Leu Ser Trp Tyr Gln Gln Lys Pro Gly
            260                 265                 270

Lys Ala Pro Lys Leu Leu Ile Tyr Glu Ala Ser Lys Leu Thr Ser Gly
            275                 280                 285

Val Pro Ser Arg Phe Ser Gly Ser Gly Ser Gly Thr Asp Phe Thr Leu
            290                 295                 300

Thr Ile Ser Ser Leu Gln Pro Glu Asp Phe Ala Thr Tyr Tyr Cys Gly
305                 310                 315                 320

Gly Gly Tyr Ser Ser Ile Ser Asp Thr Thr Phe Gly Cys Gly Thr Lys
                325                 330                 335

Val Glu Ile Lys Arg Thr
            340

<210> SEQ ID NO 3
<211> LENGTH: 220
<212> TYPE: PRT
<213> ORGANISM: Artificial Sequence
<220> FEATURE:
<223> OTHER INFORMATION: Single linker A26Fab-645dsFv (LC-vL linked)
      A26 Fab Heavy

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu

```
                  100                 105                 110
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 4
<211> LENGTH: 121
<212> TYPE: PRT
<213> ORGANISM: Artificial Sequence
<220> FEATURE:
<223> OTHER INFORMATION: Single linker A26Fab-645dsFv (LC-vL linked)
      645dsvH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 5
<211> LENGTH: 342
<212> TYPE: PRT
<213> ORGANISM: Artificial Sequence
<220> FEATURE:
<223> OTHER INFORMATION: Single linker A26Fab-645dsFv (LC-vL linked)
      A26 Fab Light-(S, 3xG4S)-645dsvL

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
```

```
            50                  55                  60
Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Ser Gly Gly Gly Ser Gly Gly Gly Gly
            210                 215                 220

Ser Gly Gly Gly Gly Ser Asp Ile Gln Met Thr Gln Ser Pro Ser Ser
225                 230                 235                 240

Val Ser Ala Ser Val Gly Asp Arg Val Thr Ile Thr Cys Gln Ser Ser
                245                 250                 255

Pro Ser Val Trp Ser Asn Phe Leu Ser Trp Tyr Gln Gln Lys Pro Gly
                260                 265                 270

Lys Ala Pro Lys Leu Leu Ile Tyr Glu Ala Ser Lys Leu Thr Ser Gly
            275                 280                 285

Val Pro Ser Arg Phe Ser Gly Ser Gly Ser Gly Thr Asp Phe Thr Leu
            290                 295                 300

Thr Ile Ser Ser Leu Gln Pro Glu Asp Phe Ala Thr Tyr Tyr Cys Gly
305                 310                 315                 320

Gly Gly Tyr Ser Ser Ile Ser Asp Thr Thr Phe Gly Cys Gly Thr Lys
                325                 330                 335

Val Glu Ile Lys Arg Thr
            340

<210> SEQ ID NO 6
<211> LENGTH: 357
<212> TYPE: PRT
<213> ORGANISM: Artificial Sequence
<220> FEATURE:
<223> OTHER INFORMATION: Single linker A26Fab-645dsFv (HC-vH linked)
      A26 Fab Heavy-(S, 3xG4S/T)-645dsvH

<400> SEQUENCE: 6

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
                20                  25                  30

Gly Ile His Trp Ile Arg Gln Ala Pro Gly Lys Gly Leu Glu Trp Val
            35                  40                  45

Ala Ser Ile Ser Pro Ser Gly Gly Leu Thr Tyr Tyr Arg Asp Ser Val
 50                  55                  60
```

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Thr Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

Gly Tyr Ser Thr Ala Pro Tyr Phe Asp Leu Trp Gly Gln Gly Thr Leu
            340                 345                 350

Val Thr Val Ser Ser
        355

<210> SEQ ID NO 7
<211> LENGTH: 214
<212> TYPE: PRT
<213> ORGANISM: Artificial Sequence
<220> FEATURE:
<223> OTHER INFORMATION: Single linker A26Fab-645dsFv (HC-vH linked)
      A26 Fab Light

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

```
Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 112
<212> TYPE: PRT
<213> ORGANISM: Artificial Sequence
<220> FEATURE:
<223> OTHER INFORMATION: Single linker A26Fab-645dsFv (HC-vH linked)
      645dsvL

<400> SEQUENCE: 8

Asp Ile Gln Met Thr Gln Ser Pro Ser Ser Val Ser Ala Ser Val Gly
 1               5                  10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
        50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gly Gly Gly Tyr Ser Ser Ile
                 85                  90                  95

Ser Asp Thr Thr Phe Gly Cys Gly Thr Lys Val Glu Ile Lys Arg Thr
            100                 105                 110

<210> SEQ ID NO 9
<211> LENGTH: 484
<212> TYPE: PRT
<213> ORGANISM: Artificial Sequence
<220> FEATURE:
<223> OTHER INFORMATION: A26Fab-645dsscFv (HC-scFv)
      A26 Fab Heavy-(S, 2xG4S/T)-645dsscFv(vH-4xG4S-vL)

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
                20                  25                  30
```

-continued

```
Gly Ile His Trp Ile Arg Gln Ala Pro Gly Lys Gly Leu Glu Trp Val
         35                  40                  45
Ala Ser Ile Ser Pro Ser Gly Gly Leu Thr Tyr Tyr Arg Asp Ser Val
     50                  55                  60
Lys Gly Arg Phe Thr Ile Ser Arg Asp Asp Ala Lys Asn Ser Pro Tyr
 65                  70                  75                  80
Leu Gln Met Asn Ser Leu Arg Ala Glu Asp Thr Ala Val Tyr Tyr Cys
                 85                  90                  95
Ala Thr Gly Gly Glu Gly Ile Phe Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Val Glu Pro Lys Ser Cys Ser Gly Gly Gly
    210                 215                 220
Gly Thr Gly Gly Gly Ser Glu Val Gln Leu Glu Ser Gly Gly
225                 230                 235                 240
Gly Leu Val Gln Pro Gly Gly Ser Leu Arg Leu Ser Cys Ala Val Ser
                245                 250                 255
Gly Ile Asp Leu Ser Asn Tyr Ala Ile Asn Trp Val Arg Gln Ala Pro
            260                 265                 270
Gly Lys Cys Leu Glu Trp Ile Gly Ile Ile Trp Ala Ser Gly Thr Thr
        275                 280                 285
Phe Tyr Ala Thr Trp Ala Lys Gly Arg Phe Thr Ile Ser Arg Asp Asn
    290                 295                 300
Ser Lys Asn Thr Val Tyr Leu Gln Met Asn Ser Leu Arg Ala Glu Asp
305                 310                 315                 320
Thr Ala Val Tyr Tyr Cys Ala Arg Thr Val Pro Gly Tyr Ser Thr Ala
                325                 330                 335
Pro Tyr Phe Asp Leu Trp Gly Gln Gly Thr Leu Val Thr Val Ser Ser
            340                 345                 350
Gly Gly Gly Gly Ser Gly Gly Gly Ser Gly Gly Gly Ser Gly
        355                 360                 365
Gly Gly Gly Ser Asp Ile Gln Met Thr Gln Ser Pro Ser Ser Val Ser
    370                 375                 380
Ala Ser Val Gly Asp Arg Val Thr Ile Thr Cys Gln Ser Ser Pro Ser
385                 390                 395                 400
Val Trp Ser Asn Phe Leu Ser Trp Tyr Gln Gln Lys Pro Gly Lys Ala
                405                 410                 415
Pro Lys Leu Leu Ile Tyr Glu Ala Ser Lys Leu Thr Ser Gly Val Pro
            420                 425                 430
Ser Arg Phe Ser Gly Ser Gly Ser Gly Thr Asp Phe Thr Leu Thr Ile
        435                 440                 445
```

Ser Ser Leu Gln Pro Glu Asp Phe Ala Thr Tyr Tyr Cys Gly Gly Gly
    450                 455                 460

Tyr Ser Ser Ile Ser Asp Thr Thr Phe Gly Cys Gly Thr Lys Val Glu
465                 470                 475                 480

Ile Lys Arg Thr

<210> SEQ ID NO 10
<211> LENGTH: 214
<212> TYPE: PRT
<213> ORGANISM: Artificial Sequence
<220> FEATURE:
<223> OTHER INFORMATION: A26Fab-645dsscFv (HC-scFv)
      A26 Fab Light

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 220
<212> TYPE: PRT
<213> ORGANISM: Artificial Sequence
<220> FEATURE:
<223> OTHER INFORMATION: A26Fab-645dsscFv (LC-scFv)
      A26 Fab Heavy

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val

```
             35                  40                  45
Ala Ser Ile Ser Pro Ser Gly Gly Leu Thr Tyr Tyr Arg Asp Ser Val
 50                  55                  60

Lys Gly Arg Phe Thr Ile Ser Arg Asp Asp Ala Lys Asn Ser Pro Tyr
 65                  70                  75                  80

Leu Gln Met Asn Ser Leu Arg Ala Glu Asp Thr Ala Val Tyr Tyr Cys
                 85                  90                  95

Ala Thr Gly Gly Glu Gly Ile Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 12
<211> LENGTH: 478
<212> TYPE: PRT
<213> ORGANISM: Artificial Sequence
<220> FEATURE:
<223> OTHER INFORMATION: A26Fab-645dsscFv (LC-scFv)
      A26 Fab Light-(S, 2xG4S)-645dsscFv(vH-4xG4S-vL)

<400> SEQUENCE: 12

Asp Ile Gln Met Thr Gln Ser Pro Ser Ser Leu Ser Ala Ser Val Gly
  1               5                  10                  15

Asp Arg Val Thr Ile Thr Cys Arg Ala Thr Gln Ser Ile Tyr Asn Ala
             20                  25                  30

Leu Ala Trp Tyr Gln Gln Lys Pro Gly Lys Ala Pro Lys Leu Leu Ile
         35                  40                  45

Tyr Asn Ala Asn Thr Leu His Thr Gly Val Pro Ser Arg Phe Ser Ala
 50                  55                  60

Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
    210                 215                 220

Ser Glu Val Gln Leu Leu Glu Ser Gly Gly Gly Leu Val Gln Pro Gly
225                 230                 235                 240

Gly Ser Leu Arg Leu Ser Cys Ala Val Ser Gly Ile Asp Leu Ser Asn
                245                 250                 255

Tyr Ala Ile Asn Trp Val Arg Gln Ala Pro Gly Lys Cys Leu Glu Trp
            260                 265                 270

Ile Gly Ile Ile Trp Ala Ser Gly Thr Thr Phe Tyr Ala Thr Trp Ala
        275                 280                 285

Lys Gly Arg Phe Thr Ile Ser Arg Asp Asn Ser Lys Asn Thr Val Tyr
    290                 295                 300

Leu Gln Met Asn Ser Leu Arg Ala Glu Asp Thr Ala Val Tyr Tyr Cys
305                 310                 315                 320

Ala Arg Thr Val Pro Gly Tyr Ser Thr Ala Pro Tyr Phe Asp Leu Trp
                325                 330                 335

Gly Gln Gly Thr Leu Val Thr Val Ser Ser Gly Gly Gly Gly Ser Gly
            340                 345                 350

Gly Gly Gly Ser Gly Gly Gly Gly Ser Gly Gly Gly Gly Ser Asp Ile
        355                 360                 365

Gln Met Thr Gln Ser Pro Ser Ser Val Ser Ala Ser Val Gly Asp Arg
    370                 375                 380

Val Thr Ile Thr Cys Gln Ser Ser Pro Ser Val Trp Ser Asn Phe Leu
385                 390                 395                 400

Ser Trp Tyr Gln Gln Lys Pro Gly Lys Ala Pro Lys Leu Leu Ile Tyr
                405                 410                 415

Glu Ala Ser Lys Leu Thr Ser Gly Val Pro Ser Arg Phe Ser Gly Ser
            420                 425                 430

Gly Ser Gly Thr Asp Phe Thr Leu Thr Ile Ser Ser Leu Gln Pro Glu
        435                 440                 445

Asp Phe Ala Thr Tyr Tyr Cys Gly Gly Gly Tyr Ser Ser Ile Ser Asp
    450                 455                 460

Thr Thr Phe Gly Cys Gly Thr Lys Val Glu Ile Lys Arg Thr
465                 470                 475
```

<210> SEQ ID NO 13
<211> LENGTH: 8
<212> TYPE: PRT
<213> ORGANISM: Artificial Sequence
<220> FEATURE:
<223> OTHER INFORMATION: Hinge linker

<400> SEQUENCE: 13

```
Asp Lys Thr His Thr Cys Ala Ala
1               5
```

<210> SEQ ID NO 14
<211> LENGTH: 11
<212> TYPE: PRT
<213> ORGANISM: Artificial Sequence
<220> FEATURE:
<223> OTHER INFORMATION: Hinge linker

<400> SEQUENCE: 14

Asp Lys Thr His Thr Cys Pro Pro Cys Pro Ala
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Hinge linker

<400> SEQUENCE: 15

Asp Lys Thr His Thr Cys Pro Pro Cys Pro Ala Thr Cys Pro Pro Cys
1               5                   10                  15

Pro Ala

<210> SEQ ID NO 16
<211> LENGTH: 25
<212> TYPE: PRT
<213> ORGANISM: Artificial Sequence
<220> FEATURE:
<223> OTHER INFORMATION: Hinge linker

<400> SEQUENCE: 16

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 17
<211> LENGTH: 30
<212> TYPE: PRT
<213> ORGANISM: Artificial Sequence
<220> FEATURE:
<223> OTHER INFORMATION: Hinge linker

<400> SEQUENCE: 17

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: HINGE LINKER

<400> SEQUENCE: 18

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 19
<211> LENGTH: 15
<212> TYPE: PRT
<213> ORGANISM: Artificial Sequence
<220> FEATURE:
<223> OTHER INFORMATION: Hinge linker

<400> SEQUENCE: 19

Asp Lys Thr His Thr Cys Cys Val Glu Cys Pro Pro Cys Pro Ala
1               5                   10                  15

```
<210> SEQ ID NO 20
<211> LENGTH: 26
<212> TYPE: PRT
<213> ORGANISM: Artificial Sequence
<220> FEATURE:
<223> OTHER INFORMATION: Hinge linker

<400> SEQUENCE: 20

Asp Lys Thr His Thr Cys Pro Arg Cys Pro Glu Pro Lys Ser Cys Asp
1               5                   10                  15
Thr Pro Pro Pro Cys Pro Arg Cys Pro Ala
            20                  25

<210> SEQ ID NO 21
<211> LENGTH: 11
<212> TYPE: PRT
<213> ORGANISM: Artificial Sequence
<220> FEATURE:
<223> OTHER INFORMATION: Hinge linker

<400> SEQUENCE: 21

Asp Lys Thr His Thr Cys Pro Ser Cys Pro Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Flexible linker

<400> SEQUENCE: 22

Ser Gly Gly Gly Gly Ser Glu
1               5

<210> SEQ ID NO 23
<211> LENGTH: 6
<212> TYPE: PRT
<213> ORGANISM: Artificial Sequence
<220> FEATURE:
<223> OTHER INFORMATION: Flexible linker

<400> SEQUENCE: 23

Asp Lys Thr His Thr Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (1)..(1)
<223> OTHER INFORMATION: S or absent

<400> SEQUENCE: 24

Xaa Gly Gly Gly Gly Ser
1               5

<210> SEQ ID NO 25
<211> LENGTH: 11
<212> TYPE: PRT
<213> ORGANISM: Artificial Sequence
<220> FEATURE:
```

```
<223> OTHER INFORMATION: Flexible linker
<220> FEATURE:
<221> NAME/KEY: Xaa
<222> LOCATION: (1)..(1)
<223> OTHER INFORMATION: S or absent

<400> SEQUENCE: 25

Xaa Gly Gly Gly Gly Ser Gly Gly Gly Gly Ser
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (1)..(1)
<223> OTHER INFORMATION: S or absent

<400> SEQUENCE: 26

Xaa Gly Gly Gly Gly Ser Gly Gly Gly Gly Ser Gly Gly Gly Gly Ser
1               5                   10                  15

<210> SEQ ID NO 27
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (1)..(1)
<223> OTHER INFORMATION: S or absent

<400> SEQUENCE: 27

Xaa Gly Gly Gly Gly Ser Gly Gly Gly Gly Ser Gly Gly Gly Gly Ser
1               5                   10                  15

Gly Gly Gly Gly Ser
            20

<210> SEQ ID NO 28
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (1)..(1)
<223> OTHER INFORMATION: S or absent

<400> SEQUENCE: 28

Xaa Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 29
<211> LENGTH: 11
<212> TYPE: PRT
<213> ORGANISM: Artificial Sequence
<220> FEATURE:
<223> OTHER INFORMATION: Flexible linker

<400> SEQUENCE: 29

Ala Ala Ala Gly Ser Gly Gly Ala Ser Ala Ser
```

<210> SEQ ID NO 30
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (7)..(7)
<223> OTHER INFORMATION: Any Amino acid

<400> SEQUENCE: 30

Ala Ala Ala Gly Ser Gly Xaa Gly Gly Gly Ser Gly Ala Ser Ala Ser
1               5                   10                  15

<210> SEQ ID NO 31
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (7)..(7)
<223> OTHER INFORMATION: Any Amino acid
<220> FEATURE:
<221> NAME/KEY: Xaa
<222> LOCATION: (12)..(12)
<223> OTHER INFORMATION: Any Amino acid

<400> SEQUENCE: 31

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 32
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (7)..(7)
<223> OTHER INFORMATION: Any Amino acid
<220> FEATURE:
<221> NAME/KEY: Xaa
<222> LOCATION: (12)..(12)
<223> OTHER INFORMATION: Any Amino acid
<220> FEATURE:
<221> NAME/KEY: Xaa
<222> LOCATION: (17)..(17)
<223> OTHER INFORMATION: Any Amino acid

<400> SEQUENCE: 32

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 33
<211> LENGTH: 31
<212> TYPE: PRT
<213> ORGANISM: Artificial Sequence
<220> FEATURE:
<223> OTHER INFORMATION: Flexible linker
<220> FEATURE:

```
<221> NAME/KEY: Xaa
<222> LOCATION: (7)..(7)
<223> OTHER INFORMATION: Any Amino acid
<220> FEATURE:
<221> NAME/KEY: Xaa
<222> LOCATION: (12)..(12)
<223> OTHER INFORMATION: Any Amino acid
<220> FEATURE:
<221> NAME/KEY: Xaa
<222> LOCATION: (17)..(17)
<223> OTHER INFORMATION: Any Amino acid
<220> FEATURE:
<221> NAME/KEY: Xaa
<222> LOCATION: (22)..(22)
<223> OTHER INFORMATION: Any Amino acid

<400> SEQUENCE: 33

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 34
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: Xaa
<222> LOCATION: (7)..(7)
<223> OTHER INFORMATION: Any Amino acid

<400> SEQUENCE: 34

Ala Ala Ala Gly Ser Gly Xaa Ser Gly Ala Ser Ala Ser
1               5                   10

<210> SEQ ID NO 35
<211> LENGTH: 28
<212> TYPE: PRT
<213> ORGANISM: Artificial Sequence
<220> FEATURE:
<223> OTHER INFORMATION: Flexible linker

<400> SEQUENCE: 35

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 36
<211> LENGTH: 11
<212> TYPE: PRT
<213> ORGANISM: Artificial Sequence
<220> FEATURE:
<223> OTHER INFORMATION: Flexible linker

<400> SEQUENCE: 36

Ala Thr Thr Thr Gly Ser Ser Pro Gly Pro Thr
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Flexible linker

<400> SEQUENCE: 37
```

```
Ala Thr Thr Thr Gly Ser
1               5

<210> SEQ ID NO 38
<211> LENGTH: 21
<212> TYPE: PRT
<213> ORGANISM: Artificial Sequence
<220> FEATURE:
<223> OTHER INFORMATION: Flexible linker

<400> SEQUENCE: 38

Glu Pro Ser Gly Pro Ile Ser Thr Ile Asn Ser Pro Pro Ser Lys Glu
1               5                   10                  15

Ser His Lys Ser Pro
            20

<210> SEQ ID NO 39
<211> LENGTH: 15
<212> TYPE: PRT
<213> ORGANISM: Artificial Sequence
<220> FEATURE:
<223> OTHER INFORMATION: Flexible linker

<400> SEQUENCE: 39

Gly Thr Val Ala Ala Pro Ser Val Phe Ile Phe Pro Pro Ser Asp
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Flexible linker

<400> SEQUENCE: 40

Gly Gly Gly Gly Ile Ala Pro Ser Met Val Gly Gly Gly Gly Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Flexible linker

<400> SEQUENCE: 41

Gly Gly Gly Gly Lys Val Glu Gly Ala Gly Gly Gly Gly Gly Ser
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Flexible linker

<400> SEQUENCE: 42

Gly Gly Gly Gly Ser Met Lys Ser His Asp Gly Gly Gly Gly Ser
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Flexible linker
```

<400> SEQUENCE: 43

Gly Gly Gly Gly Asn Leu Ile Thr Ile Val Gly Gly Gly Gly Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Flexible linker

<400> SEQUENCE: 44

Gly Gly Gly Gly Val Val Pro Ser Leu Pro Gly Gly Gly Gly Ser
1               5                   10                  15

<210> SEQ ID NO 45
<211> LENGTH: 12
<212> TYPE: PRT
<213> ORGANISM: Artificial Sequence
<220> FEATURE:
<223> OTHER INFORMATION: Flexible linker

<400> SEQUENCE: 45

Gly Gly Glu Lys Ser Ile Pro Gly Gly Gly Gly Ser
1               5                   10

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

Arg Pro Leu Ser Tyr Arg Pro Pro Phe Pro Phe Gly Phe Pro Ser Val
1               5                   10                  15

Arg Pro

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

Tyr Pro Arg Ser Ile Tyr Ile Arg Arg Arg His Pro Ser Pro Ser Leu
1               5                   10                  15

Thr Thr

<210> SEQ ID NO 48
<211> LENGTH: 18
<212> TYPE: PRT
<213> ORGANISM: Artificial Sequence
<220> FEATURE:
<223> OTHER INFORMATION: Flexible linker

<400> SEQUENCE: 48

Thr Pro Ser His Leu Ser His Ile Leu Pro Ser Phe Gly Leu Pro Thr
1               5                   10                  15

Phe Asn

<210> SEQ ID NO 49

```
<211> LENGTH: 18
<212> TYPE: PRT
<213> ORGANISM: Artificial Sequence
<220> FEATURE:
<223> OTHER INFORMATION: Flexible linker

<400> SEQUENCE: 49

Arg Pro Val Ser Pro Phe Thr Phe Pro Arg Leu Ser Asn Ser Trp Leu
1               5                   10                  15

Pro Ala

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Ser Pro Ala Ala His Phe Pro Arg Ser Ile Pro Arg Pro Gly Pro Ile
1               5                   10                  15

Arg Thr

<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Ala Pro Gly Pro Ser Ala Pro Ser His Arg Ser Leu Pro Ser Arg Ala
1               5                   10                  15

Phe Gly

<210> SEQ ID NO 52
<211> LENGTH: 18
<212> TYPE: PRT
<213> ORGANISM: Artificial Sequence
<220> FEATURE:
<223> OTHER INFORMATION: Flexible linker

<400> SEQUENCE: 52

Pro Arg Asn Ser Ile His Phe Leu His Pro Leu Leu Val Ala Pro Leu
1               5                   10                  15

Gly Ala

<210> SEQ ID NO 53
<211> LENGTH: 18
<212> TYPE: PRT
<213> ORGANISM: Artificial Sequence
<220> FEATURE:
<223> OTHER INFORMATION: Flexible linker

<400> SEQUENCE: 53

Met Pro Ser Leu Ser Gly Val Leu Gln Val Arg Tyr Leu Ser Pro Pro
1               5                   10                  15

Asp Leu

<210> SEQ ID NO 54
<211> LENGTH: 18
<212> TYPE: PRT
<213> ORGANISM: Artificial Sequence
<220> FEATURE:
```

```
<223> OTHER INFORMATION: Flexible linker

<400> SEQUENCE: 54

Ser Pro Gln Tyr Pro Ser Pro Leu Thr Leu Thr Leu Pro Pro His Pro
1               5                   10                  15

Ser Leu

<210> SEQ ID NO 55
<211> LENGTH: 18
<212> TYPE: PRT
<213> ORGANISM: Artificial Sequence
<220> FEATURE:
<223> OTHER INFORMATION: Flexible linker

<400> SEQUENCE: 55

Asn Pro Ser Leu Asn Pro Pro Ser Tyr Leu His Arg Ala Pro Ser Arg
1               5                   10                  15

Ile Ser

<210> SEQ ID NO 56
<211> LENGTH: 17
<212> TYPE: PRT
<213> ORGANISM: Artificial Sequence
<220> FEATURE:
<223> OTHER INFORMATION: Flexible linker

<400> SEQUENCE: 56

Leu Pro Trp Arg Thr Ser Leu Leu Pro Ser Leu Pro Leu Arg Arg Arg
1               5                   10                  15

Pro

<210> SEQ ID NO 57
<211> LENGTH: 18
<212> TYPE: PRT
<213> ORGANISM: Artificial Sequence
<220> FEATURE:
<223> OTHER INFORMATION: Flexible linker

<400> SEQUENCE: 57

Pro Pro Leu Phe Ala Lys Gly Pro Val Gly Leu Leu Ser Arg Ser Phe
1               5                   10                  15

Pro Pro

<210> SEQ ID NO 58
<211> LENGTH: 18
<212> TYPE: PRT
<213> ORGANISM: Artificial Sequence
<220> FEATURE:
<223> OTHER INFORMATION: Flexible linker

<400> SEQUENCE: 58

Val Pro Pro Ala Pro Val Val Ser Leu Arg Ser Ala His Ala Arg Pro
1               5                   10                  15

Pro Tyr

<210> SEQ ID NO 59
<211> LENGTH: 17
<212> TYPE: PRT
<213> ORGANISM: Artificial Sequence
<220> FEATURE:
<223> OTHER INFORMATION: Flexible linker

<400> SEQUENCE: 59
```

```
Leu Arg Pro Thr Pro Pro Arg Val Arg Ser Tyr Thr Cys Cys Pro Thr
1               5                   10                  15

Pro

<210> SEQ ID NO 60
<211> LENGTH: 18
<212> TYPE: PRT
<213> ORGANISM: Artificial Sequence
<220> FEATURE:
<223> OTHER INFORMATION: Flexible linker

<400> SEQUENCE: 60

Pro Asn Val Ala His Val Leu Pro Leu Leu Thr Val Pro Trp Asp Asn
1               5                   10                  15

Leu Arg

<210> SEQ ID NO 61
<211> LENGTH: 18
<212> TYPE: PRT
<213> ORGANISM: Artificial Sequence
<220> FEATURE:
<223> OTHER INFORMATION: Flexible linker

<400> SEQUENCE: 61

Cys Asn Pro Leu Leu Pro Leu Cys Ala Arg Ser Pro Ala Val Arg Thr
1               5                   10                  15

Phe Pro

<210> SEQ ID NO 62
<211> LENGTH: 11
<212> TYPE: PRT
<213> ORGANISM: Artificial Sequence
<220> FEATURE:
<223> OTHER INFORMATION: rigid linker

<400> SEQUENCE: 62

Gly Ala Pro Ala Pro Ala Ala Pro Ala Pro Ala
1               5                   10

<210> SEQ ID NO 63
<211> LENGTH: 4
<212> TYPE: PRT
<213> ORGANISM: Artificial Sequence
<220> FEATURE:
<223> OTHER INFORMATION: rigid linker

<400> SEQUENCE: 63

Pro Pro Pro Pro
1

<210> SEQ ID NO 64
<211> LENGTH: 11
<212> TYPE: PRT
<213> ORGANISM: Artificial Sequence
<220> FEATURE:
<223> OTHER INFORMATION: albumin binding peptides

<400> SEQUENCE: 64

Asp Leu Cys Leu Arg Asp Trp Gly Cys Leu Trp
1               5                   10

<210> SEQ ID NO 65
<211> LENGTH: 11
<212> TYPE: PRT
<213> ORGANISM: Artificial Sequence
```

```
<220> FEATURE:
<223> OTHER INFORMATION: albumin binding peptides

<400> SEQUENCE: 65

Asp Ile Cys Leu Pro Arg Trp Gly Cys Leu Trp
1               5                   10

<210> SEQ ID NO 66
<211> LENGTH: 15
<212> TYPE: PRT
<213> ORGANISM: Artificial Sequence
<220> FEATURE:
<223> OTHER INFORMATION: albumin binding peptides

<400> SEQUENCE: 66

Met Glu Asp Ile Cys Leu Pro Arg Trp Gly Cys Leu Trp Gly Asp
1               5                   10                  15

<210> SEQ ID NO 67
<211> LENGTH: 20
<212> TYPE: PRT
<213> ORGANISM: Artificial Sequence
<220> FEATURE:
<223> OTHER INFORMATION: albumin binding peptides

<400> SEQUENCE: 67

Gln Arg Leu Met Glu Asp Ile Cys Leu Pro Arg Trp Gly Cys Leu Trp
1               5                   10                  15

Glu Asp Asp Glu
            20

<210> SEQ ID NO 68
<211> LENGTH: 20
<212> TYPE: PRT
<213> ORGANISM: Artificial Sequence
<220> FEATURE:
<223> OTHER INFORMATION: albumin binding peptides

<400> SEQUENCE: 68

Gln Gly Leu Ile Gly Asp Ile Cys Leu Pro Arg Trp Gly Cys Leu Trp
1               5                   10                  15

Gly Arg Ser Val
            20

<210> SEQ ID NO 69
<211> LENGTH: 21
<212> TYPE: PRT
<213> ORGANISM: Artificial Sequence
<220> FEATURE:
<223> OTHER INFORMATION: albumin binding peptides

<400> SEQUENCE: 69

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 70
<211> LENGTH: 15
<212> TYPE: PRT
<213> ORGANISM: Artificial Sequence
<220> FEATURE:
<223> OTHER INFORMATION: albumin binding peptides

<400> SEQUENCE: 70
```

```
Glu Asp Ile Cys Leu Pro Arg Trp Gly Cys Leu Trp Glu Asp Asp
1               5                   10                  15
```

<210> SEQ ID NO 71
<211> LENGTH: 18
<212> TYPE: PRT
<213> ORGANISM: Artificial Sequence
<220> FEATURE:
<223> OTHER INFORMATION: albumin binding peptides

<400> SEQUENCE: 71

```
Arg Leu Met Glu Asp Ile Cys Leu Pro Arg Trp Gly Cys Leu Trp Glu
1               5                   10                  15

Asp Asp
```

<210> SEQ ID NO 72
<211> LENGTH: 16
<212> TYPE: PRT
<213> ORGANISM: Artificial Sequence
<220> FEATURE:
<223> OTHER INFORMATION: albumin binding peptides

<400> SEQUENCE: 72

```
Met Glu Asp Ile Cys Leu Pro Arg Trp Gly Cys Leu Trp Glu Asp Asp
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: albumin binding peptides

<400> SEQUENCE: 73

```
Met Glu Asp Ile Cys Leu Pro Arg Trp Gly Cys Leu Trp Glu Asp
1               5                   10                  15
```

<210> SEQ ID NO 74
<211> LENGTH: 18
<212> TYPE: PRT
<213> ORGANISM: Artificial Sequence
<220> FEATURE:
<223> OTHER INFORMATION: albumin binding peptides

<400> SEQUENCE: 74

```
Arg Leu Met Glu Asp Ile Cys Leu Ala Arg Trp Gly Cys Leu Trp Glu
1               5                   10                  15

Asp Asp
```

<210> SEQ ID NO 75
<211> LENGTH: 20
<212> TYPE: PRT
<213> ORGANISM: Artificial Sequence
<220> FEATURE:
<223> OTHER INFORMATION: albumin binding peptides

<400> SEQUENCE: 75

```
Glu Val Arg Ser Phe Cys Thr Arg Trp Pro Ala Glu Lys Ser Cys Lys
1               5                   10                  15

Pro Leu Arg Gly
            20
```

<210> SEQ ID NO 76
<211> LENGTH: 20
<212> TYPE: PRT

```
<213> ORGANISM: Artificial Sequence
<220> FEATURE:
<223> OTHER INFORMATION: albumin binding peptides

<400> SEQUENCE: 76

Arg Ala Pro Glu Ser Phe Val Cys Tyr Trp Glu Thr Ile Cys Phe Glu
1               5                   10                  15

Arg Ser Glu Gln
            20

<210> SEQ ID NO 77
<211> LENGTH: 11
<212> TYPE: PRT
<213> ORGANISM: Artificial Sequence
<220> FEATURE:
<223> OTHER INFORMATION: albumin binding peptides

<400> SEQUENCE: 77

Glu Met Cys Tyr Phe Pro Gly Ile Cys Trp Met
1               5                   10

<210> SEQ ID NO 78
<211> LENGTH: 16
<212> TYPE: PRT
<213> ORGANISM: Artificial Sequence
<220> FEATURE:
<223> OTHER INFORMATION: A26 heavy chain flexible linker

<400> SEQUENCE: 78

Ser Gly Gly Gly Gly Ser Gly Gly Gly Gly Thr Gly Gly Gly Gly Ser
1               5                   10                  15

<210> SEQ ID NO 79
<211> LENGTH: 20
<212> TYPE: PRT
<213> ORGANISM: Artificial Sequence
<220> FEATURE:
<223> OTHER INFORMATION: flexible linker

<400> SEQUENCE: 79

Gly Gly Gly Gly Ser Gly Gly Gly Gly Ser Gly Gly Gly Gly Ser Gly
1               5                   10                  15

Gly Gly Gly Ser
            20

<210> SEQ ID NO 80
<211> LENGTH: 11
<212> TYPE: PRT
<213> ORGANISM: Artificial Sequence
<220> FEATURE:
<223> OTHER INFORMATION: A26 heavy chain flexible linker

<400> SEQUENCE: 80

Ser Gly Gly Gly Gly Thr Gly Gly Gly Gly Ser
1               5                   10

<210> SEQ ID NO 81
<211> LENGTH: 214
<212> TYPE: PRT
<213> ORGANISM: Artificial Sequence
<220> FEATURE:
<223> OTHER INFORMATION: Fab LC

<400> SEQUENCE: 81

Asp Ile Gln Met Thr Gln Ser Pro Ser Ser Leu Ser Ala Ser Val Gly
1               5                   10                  15
```

```
Asp Arg Val Thr Ile Thr Cys Arg Ala Thr Gln Ser Ile Tyr Asn Ala
         20                  25                  30

Leu Ala Trp Tyr Gln Gln Lys Pro Gly Lys Ala Pro Lys Leu Leu Ile
             35                  40                  45

Tyr Asn Ala Asn Thr Leu His Thr Gly Val Pro Ser Arg Phe Ser Ala
 50                      55                  60

Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 356
<212> TYPE: PRT
<213> ORGANISM: Artificial Sequence
<220> FEATURE:
<223> OTHER INFORMATION: Fab-648gH1 HC

<400> SEQUENCE: 82

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
             20                  25                  30

Gly Ile His Trp Ile Arg Gln Ala Pro Gly Lys Gly Leu Glu Trp Val
         35                  40                  45

Ala Ser Ile Ser Pro Ser Gly Gly Leu Thr Tyr Tyr Arg Asp Ser Val
 50                  55                  60

Lys Gly Arg Phe Thr Ile Ser Arg Asp Asp Ala Lys Asn Ser Pro Tyr
 65                  70                  75                  80

Leu Gln Met Asn Ser Leu Arg Ala Glu Asp Thr Ala Val Tyr Tyr Cys
                 85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Thr Gly Gly Gly Ser Glu Val Gln Leu
225                 230                 235                 240

Val Glu Ser Gly Gly Gly Leu Val Gln Pro Gly Gly Ser Leu Arg Leu
                245                 250                 255

Ser Cys Ala Val Ser Gly Phe Ser Leu Ser Arg Tyr Ala Met Thr Trp
            260                 265                 270

Val Arg Gln Ala Pro Gly Lys Cys Leu Glu Trp Ile Gly Thr Ile Thr
        275                 280                 285

Thr Gly Gly Asn Thr Asn Tyr Ala Asn Trp Ala Lys Gly Arg Phe Thr
    290                 295                 300

Ile Ser Lys Asp Ser Thr Thr Val Tyr Leu Gln Met Asn Ser Leu Arg
305                 310                 315                 320

Ala Glu Asp Thr Ala Val Tyr Tyr Cys Ala Arg Gly Gly Tyr Val Ser
                325                 330                 335

Tyr Ala Asp Ala Thr Glu Leu Ser Leu Trp Gly Gln Gly Thr Leu Val
            340                 345                 350

Thr Val Ser Ser
        355

<210> SEQ ID NO 83
<211> LENGTH: 112
<212> TYPE: PRT
<213> ORGANISM: Artificial Sequence
<220> FEATURE:
<223> OTHER INFORMATION: synthetic-648gL1

<400> SEQUENCE: 83

Asp Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Ser Arg
            20                  25                  30

Leu Ala Trp Tyr Gln Gln Lys Pro Gly Lys Ala Pro Lys Leu Leu Ile
        35                  40                  45

Tyr Tyr Ala Ser Thr Val Ala Ser Gly Val Pro Ser Arg Phe Lys Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asp Tyr Ser Ser Ser
                85                  90                  95

Ser Ser Tyr Ala Phe Gly Cys Gly Thr Lys Val Glu Ile Lys Arg Thr
            100                 105                 110

<210> SEQ ID NO 84
<211> LENGTH: 220
<212> TYPE: PRT
<213> ORGANISM: Artificial Sequence
<220> FEATURE:
<223> OTHER INFORMATION: Fab HC
```

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 85
<211> LENGTH: 342
<212> TYPE: PRT
<213> ORGANISM: Artificial Sequence
<220> FEATURE:
<223> OTHER INFORMATION: Fab-648gL1 LC

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala

-continued

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Ser Gly Gly Gly Ser Gly Gly Gly Gly
            210                 215                 220

Ser Gly Gly Gly Ser Asp Ile Val Met Thr Gln Ser Pro Ser Thr
225                 230                 235                 240

Leu Ser Ala Ser Val Gly Asp Arg Val Thr Ile Thr Cys Gln Ala Ser
                245                 250                 255

Gln Ser Ile Gly Ser Arg Leu Ala Trp Tyr Gln Gln Lys Pro Gly Lys
                260                 265                 270

Ala Pro Lys Leu Leu Ile Tyr Tyr Ala Ser Thr Val Ala Ser Gly Val
                275                 280                 285

Pro Ser Arg Phe Lys Gly Ser Gly Ser Gly Thr Glu Phe Thr Leu Thr
290                 295                 300

Ile Ser Ser Leu Gln Pro Asp Asp Phe Ala Thr Tyr Tyr Cys Gln Ser
305                 310                 315                 320

Tyr Asp Tyr Ser Ser Ser Ser Tyr Ala Phe Gly Cys Gly Thr Lys
                325                 330                 335

Val Glu Ile Lys Arg Thr
            340

<210> SEQ ID NO 86
<211> LENGTH: 120
<212> TYPE: PRT
<213> ORGANISM: Artificial Sequence
<220> FEATURE:
<223> OTHER INFORMATION: synthetic-648gH1

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Arg Tyr
                20                  25                  30

Ala Met Thr Trp Val Arg Gln Ala Pro Gly Lys Cys Leu Glu Trp Ile
            35                  40                  45

Gly Thr Ile Thr Thr Gly Gly Asn Thr Asn Tyr Ala Asn Trp Ala Lys
50                  55                  60

Gly Arg Phe Thr Ile Ser Lys Asp Ser Thr Thr Val Tyr Leu Gln Met
65                  70                  75                  80

Asn Ser Leu Arg Ala Glu Asp Thr Ala Val Tyr Tyr Cys Ala Arg Gly
                85                  90                  95

Gly Tyr Val Ser Tyr Ala Asp Ala Thr Glu Leu Ser Leu Trp Gly Gln
            100                 105                 110

Gly Thr Leu Val Thr Val Ser Ser
        115                 120

<210> SEQ ID NO 87
<211> LENGTH: 10
<212> TYPE: PRT
```

```
<213> ORGANISM: Artificial
<220> FEATURE:
<223> OTHER INFORMATION: 645 CDRH1

<400> SEQUENCE: 87

Gly Ile Asp Leu Ser Asn Tyr Ala Ile Asn
1               5                   10

<210> SEQ ID NO 88
<211> LENGTH: 16
<212> TYPE: PRT
<213> ORGANISM: Artificial
<220> FEATURE:
<223> OTHER INFORMATION: 645 CDRH2

<400> SEQUENCE: 88

Ile Ile Trp Ala Ser Gly Thr Thr Phe Tyr Ala Thr Trp Ala Lys Gly
1               5                   10                  15

<210> SEQ ID NO 89
<211> LENGTH: 13
<212> TYPE: PRT
<213> ORGANISM: Artificial
<220> FEATURE:
<223> OTHER INFORMATION: 645 CDRH3

<400> SEQUENCE: 89

Thr Val Pro Gly Tyr Ser Thr Ala Pro Tyr Phe Asp Leu
1               5                   10

<210> SEQ ID NO 90
<211> LENGTH: 12
<212> TYPE: PRT
<213> ORGANISM: Artificial
<220> FEATURE:
<223> OTHER INFORMATION: 645 CDRL1

<400> SEQUENCE: 90

Gln Ser Ser Pro Ser Val Trp Ser Asn Phe Leu Ser
1               5                   10

<210> SEQ ID NO 91
<211> LENGTH: 7
<212> TYPE: PRT
<213> ORGANISM: Artificial
<220> FEATURE:
<223> OTHER INFORMATION: 645 CDRL2

<400> SEQUENCE: 91

Glu Ala Ser Lys Leu Thr Ser
1               5

<210> SEQ ID NO 92
<211> LENGTH: 11
<212> TYPE: PRT
<213> ORGANISM: Artificial
<220> FEATURE:
<223> OTHER INFORMATION: 645 CDRL3

<400> SEQUENCE: 92

Gly Gly Gly Tyr Ser Ser Ile Ser Asp Thr Thr
1               5                   10

<210> SEQ ID NO 93
<211> LENGTH: 10
<212> TYPE: PRT
<213> ORGANISM: Artificial
```

```
<220> FEATURE:
<223> OTHER INFORMATION: 648 CDRH1

<400> SEQUENCE: 93

Gly Phe Ser Leu Ser Arg Tyr Ala Met Thr
1               5                   10

<210> SEQ ID NO 94
<211> LENGTH: 16
<212> TYPE: PRT
<213> ORGANISM: Artificial
<220> FEATURE:
<223> OTHER INFORMATION: 648 CRDH2

<400> SEQUENCE: 94

Thr Ile Thr Thr Gly Gly Asn Thr Asn Tyr Ala Asn Trp Ala Lys Gly
1               5                   10                  15

<210> SEQ ID NO 95
<211> LENGTH: 14
<212> TYPE: PRT
<213> ORGANISM: Artificial
<220> FEATURE:
<223> OTHER INFORMATION: 648 CRDH3

<400> SEQUENCE: 95

Gly Gly Tyr Val Ser Tyr Ala Asp Ala Thr Glu Leu Ser Leu
1               5                   10

<210> SEQ ID NO 96
<211> LENGTH: 11
<212> TYPE: PRT
<213> ORGANISM: Artificial
<220> FEATURE:
<223> OTHER INFORMATION: 648 CDRL1

<400> SEQUENCE: 96

Gln Ala Ser Gln Ser Ile Gly Ser Arg Leu Ala
1               5                   10

<210> SEQ ID NO 97
<211> LENGTH: 7
<212> TYPE: PRT
<213> ORGANISM: Artificial
<220> FEATURE:
<223> OTHER INFORMATION: 648 CDRL2

<400> SEQUENCE: 97

Tyr Ala Ser Thr Val Ala Ser
1               5

<210> SEQ ID NO 98
<211> LENGTH: 12
<212> TYPE: PRT
<213> ORGANISM: Artificial
<220> FEATURE:
<223> OTHER INFORMATION: 648 CDRL3

<400> SEQUENCE: 98

Gln Ser Tyr Asp Tyr Ser Ser Ser Ser Ser Tyr Ala
1               5                   10

<210> SEQ ID NO 99
<211> LENGTH: 121
<212> TYPE: PRT
<213> ORGANISM: Artificial
<220> FEATURE:
```

<223> OTHER INFORMATION: Heavy chain variable domain of anti-albumin
    antibody (no ds)

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 100
<211> LENGTH: 121
<212> TYPE: PRT
<213> ORGANISM: Artificial
<220> FEATURE:
<223> OTHER INFORMATION: b) Heavy chain variable domain of anti-albumin
    antibody (ds)

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 101
<211> LENGTH: 112
<212> TYPE: PRT
<213> ORGANISM: Artificial
<220> FEATURE:
<223> OTHER INFORMATION: (c) Light chain variable domain of anti-albumin
    antibody (no ds)

<400> SEQUENCE: 101

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn

```
                    20                  25                  30
Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys Arg Thr
                100                 105                 110

<210> SEQ ID NO 102
<211> LENGTH: 112
<212> TYPE: PRT
<213> ORGANISM: Artificial
<220> FEATURE:
<223> OTHER INFORMATION: d) Light chain variable domain of anti-albumin
      antibody (ds)

<400> SEQUENCE: 102

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Cys Gly Thr Lys Val Glu Ile Lys Arg Thr
                100                 105                 110

<210> SEQ ID NO 103
<211> LENGTH: 16
<212> TYPE: PRT
<213> ORGANISM: Artificial
<220> FEATURE:
<223> OTHER INFORMATION: Linker sequence

<400> SEQUENCE: 103

Ser Gly Gly Gly Gly Ser Gly Gly Gly Ser Gly Gly Gly Gly Ser
1               5                   10                  15

<210> SEQ ID NO 104
<211> LENGTH: 11
<212> TYPE: PRT
<213> ORGANISM: Artificial
<220> FEATURE:
<223> OTHER INFORMATION: Linker sequence

<400> SEQUENCE: 104

Ser Gly Gly Gly Gly Ser Gly Gly Gly Gly Ser
1               5                   10
```

SINGLE LINKER FABFV ANTIBODIES AND METHODS OF PRODUCING SAME

This application is a US national phase of International Application No. PCT/EP2013/077758, filed on Dec. 20, 2013, which claims the benefit of Great Britain patent application 1223276.5, filed Dec. 21, 2012.

The present disclosure relates to certain multi-specific constructs, pharmaceutical formulations comprising the construct, DNA encoding the constructs and vectors comprising same. The disclosure also extends to a method of expressing the constructs, for example in a host cell and methods for formulating same as a pharmaceutical composition. The disclosure also relates to use of the constructs and formulations in treatment.

WO2009/040562 and WO2010/035012 discloses certain bi-specific molecules useful as therapeutic agents, known as Fab-Fv or Fab-dsFv respectively. The molecules of this type have good binding affinity for the antigens to which they are specific and no significant occlusion of antigen binding sites occurs in the format. Whilst a high percentage of these antibody molecules are expressed as functional monomer there is a proportion that aggregates and from which the monomer needs to be purified.

The present inventors have re-engineered the molecules concerned to provide molecules with equivalent functionality, whilst minimising aggregation at the expression stage and thus substantially increasing the yield of monomer.

In one embodiment there is provided a multi-specific antibody molecule comprising or consisting of three polypeptides:
a) a polypeptide chain of formula (I):

$(Vxx)_n Vx-Cx-X-V_1$; and b) a polypeptide chain of formula (II):

$(Vyy)_n Vy-C_y$ c) a polypeptide of formula (III):

$V_2$ wherein
Vx represents a variable domain,
Vxx represents a variable domain,
Cx represents a constant region domain,
X represents a linker,
$V_1$ represents a variable domain,
Vy represents a variable domain,
Vyy represents a variable domain,
Cy represents a constant region domain,
$V_2$ represents a variable domain,
n independently represents 0 or 1,
wherein the polypeptide chain of formula (I) and the polypeptide chain of formula (II) are aligned such that the constant regions Cx and Cy are paired and the variable domain Vx and Vy are paired to form a binding domain and optionally a disulphide bond is present between $V_1$ and $V_2$, in particular where a disulphide bond is present.

In one embodiment Vxx and Vyy are also paired to form a binding domain.

In one embodiment a disulphide bond is present between $V_1$ and $V_2$.

In one embodiment there is provided a bi-specific antibody molecule comprising or consisting of three polypeptides;
a) a heavy chain of formula (Ia):

$VH-CH_1-X-V_1$; and b) a light chain of formula (IIa):

$VL-C_L$ c) a polypeptide of formula (III):

$V_2$ wherein
VH represents a heavy chain variable domain,
$CH_1$ represents domain 1 of a heavy chain constant region,
X represents a linker,
$V_1$ represents a variable domain,
$V_L$ represents a light chain variable domain,
$C_L$ represents a constant region from a light chain,
$V_2$ represents a variable domain,
wherein optionally a disulphide bond is present between $V_1$ and $V_2$, in particular where a disulphide bond is present.

In one embodiment there is provided a bi-specific antibody molecule comprising or consisting of three polypeptides;
a) a heavy chain of formula (Ib):

$VH-CH_1$; and b) a light chain of formula (IIb):

$VL-C_L-X-V_2$ c) a polypeptide of formula (III):

$V_1$ wherein
VH represents a heavy chain variable domain,
$CH_1$ represents domain 1 of a heavy chain constant region,
X represents a linker,
$V_1$ represents a variable domain,
$V_L$ represents a light chain variable domain,
$C_L$ represents a constant region from a light chain,
$V_2$ represents a variable domain,
wherein optionally a disulphide bond is present between $V_1$ and $V_2$, in particular where a disulphide bond is present.

In one embodiment a disulphide bond is present between $V_1$ and $V_2$.

Advantageously, the present construct minimises the amount of aggregation seen during expression and maximises the amount of monomer obtained, for example the monomer may be 50%, 60%, 70% or 75% or more such as 80 or 90% or more of the protein expressed.

BRIEF DESCRIPTION OF THE FIGURES

FIG. 1 shows various sequences for single linker Fab-Fv constructs according to the invention and comparator constructs Fabdsscfv and FabdsFv FIG. 2 shows SDS-PAGE analysis of the various constructs FIG. 5 shows transient expression of single linker Fab-dsFvs expressed from triple gene plasmids in CHO cells.

FIG. 6 shows SDS-PAGE analysis of various single linker Fab-dsFvs expressed from triple gene plasmids.

FIG. 7 shows size exclusion analysis of single linker Fab-dsFv expressed from a triple gene plasmids.

DETAILED DESCRIPTION OF THE INVENTION

Figure 3:
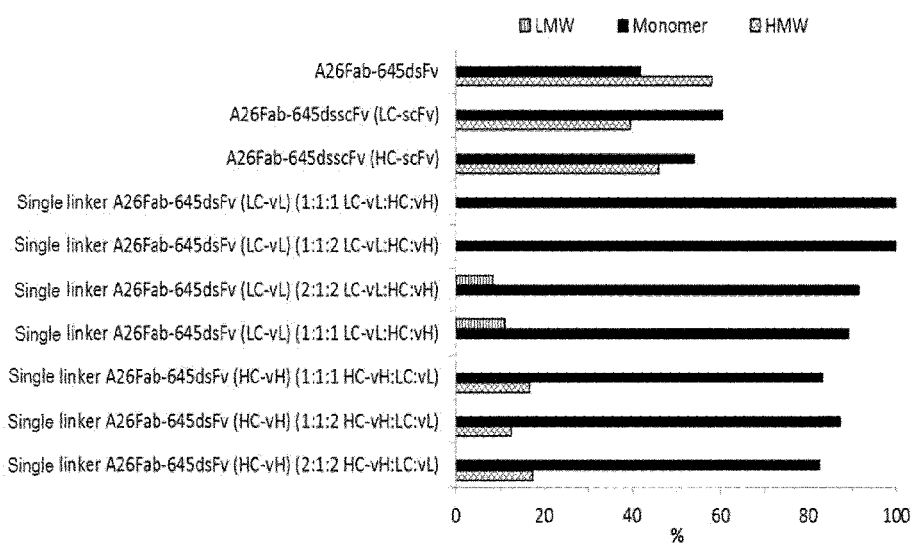
FIG. 3 shows size exclusion analysis of various constructs
Figure 4:
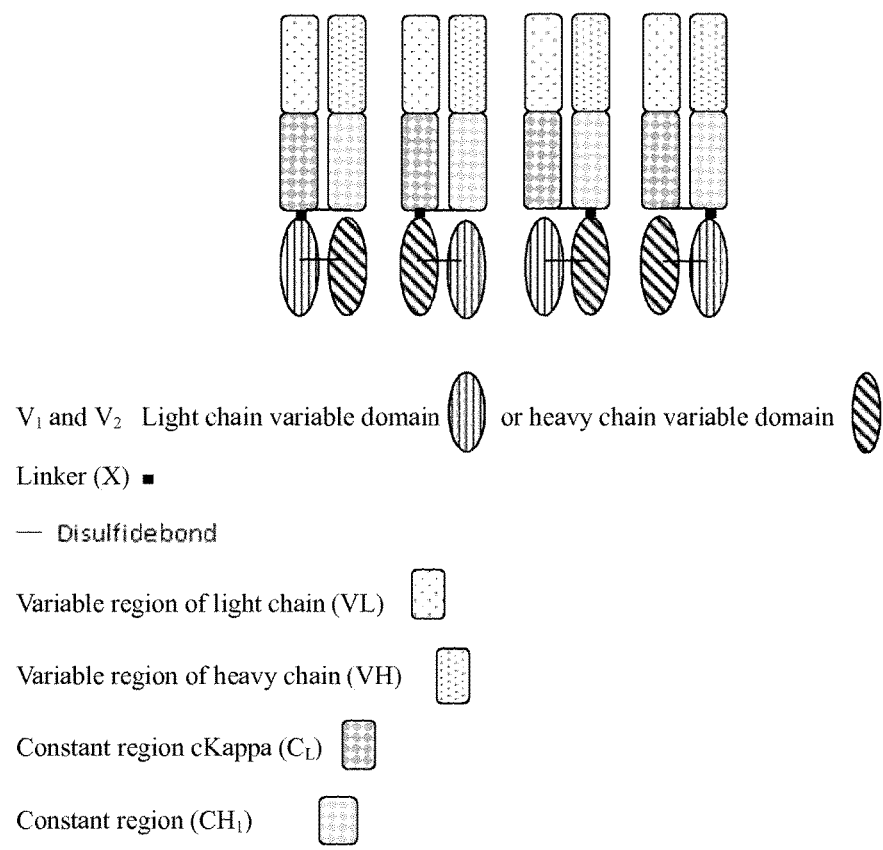
FIG. 4 shows a diagrammatic representation of various example constructs according to the disclosure

Multi-specific antibody as employed herein refers to an antibody molecule as described herein which has two or more binding domains, for example two or three binding domains. In one embodiment the construct is a tri-specific antibody. Tri-specific molecule as employed herein refers to a molecule with three antigen binding sites, which may independently bind the same or different antigens.

In one embodiment the construct is a bi-specific antibody. Bi-specific molecule as employed herein refers to a molecule with two antigen binding sites, which may bind the same or different antigens.

In one embodiment the domains all bind the same antigen, including binding the same epitope on the antigen or binding different epitopes on the antigen.

In one embodiment there are three binding domains and each of the three binding domains bind different (distinct) antigens.

In one embodiment there are three binding domains and two binding domains bind the same antigen, including binding the same epitope or different epitopes on the same antigen, and the third binding domain binds a different (distinct) antigen.

In one embodiment the present disclosure relates to a bi-specific antibody comprising or consisting of three polypeptide chains.

The multi-specific molecules according to the present disclosure are provided as a dimer of a heavy and light chain of:

formula (I) and (II) respectively, wherein the Vx-Cx portion together with the Vy-Cy portion form a functional Fab or Fab' fragment, or alternatively formula (Ia) and (IIa), wherein the VH-$CH_1$ portion together with the VL-$C_L$ form a functional Fab or Fab' fragment.

In one embodiment the construct of the present disclosure has only two antigen binding sites.

Antigen binding site as employed herein refers to a portion of the molecule, which comprises a pair of variable regions, in particular a cognate pair, that interact specifically with the target antigen.

Specifically as employed herein is intended to refer to a binding site that only recognises the antigen to which it is specific or a binding site that has significantly higher binding affinity to the antigen to which is specific compared to affinity to antigens to which it is non-specific, for example 5, 6, 7, 8, 9, 10 times higher binding affinity.

Binding affinity may be measured by standard assay, for example surface plasmon resonance, such as BIAcore.

In one embodiment one or more natural or engineered inter chain (i.e. inter light and heavy chain) disulphide bonds are present in the functional Fab or Fab' fragment.

In one embodiment a "natural" disulfide bond is present between a $CH_1$ and $C_L$ or corresponding components Cx and Cy in the polypeptide chains of formula (I) and (II). Below references to $CH_1$ may apply equally to Cx. Below references to $C_L$ may apply equally to Cy.

When the $C_L$ domain is derived from either Kappa or Lambda the natural position for a bond forming cysteine is 214 in human cKappa and cLambda (Kabat numbering 4$^{th}$ edition 1987).

The exact location of the disulfide bond forming cysteine in $CH_1$ depends on the particular domain actually employed. Thus, for example in human gamma-1 the natural position of the disulfide bond is located at position 233 (Kabat numbering 4$^{th}$ edition 1987). The position of the bond forming cysteine for other human isotypes such as gamma 2, 3, 4, IgM and IgD are known, for example position 127 for human IgM, IgE, IgG2, IgG3, IgG4 and 128 of the heavy chain of human IgD and IgA2B.

A disulfide bond or bond(s) in the constant region of the molecule may be in addition to the optional disulfide bond between a variable domain pair $V_1$ and $V_2$.

In one embodiment the multi-specific antibody according to the disclosure has a disulfide bond in a position equivalent or corresponding to that in the naturally occurring between $CH_1$ and $C_L$.

In one embodiment a constant region comprising $CH_1$ and a constant region such as $C_L$ has a disulfide bond which is in a non-naturally occurring position. This may be engineered into the molecule by introducing cysteine(s) into the amino acid chain at the position or positions required. This non-natural disulfide bond is in addition to or as an alternative to the natural disulfide bond present between $CH_1$ and $C_L$.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N Y, 1989; Ausbel et al., Current Protocols in Molecular Biology, Greene Publishing & Wiley-Interscience, N Y, 1993). Site-directed mutagenesis kits are commercially available, e.g. QuikChange® Site-Directed Mutagenesis kit (Stratagene, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

In one embodiment a disulfide bond between $CH_1$ and $C_L$ is completely absent, for example the interchain cysteines may be replaced by another amino acid, such as serine. Thus there are no inter chain disulphide bonds in the functional Fab fragment of the molecule. Disclosures such as WO2005/003170, incorporated herein by reference, describe how to provide Fab fragments without an inter chain disulphide bond.

In one embodiment n is 1 in the polypeptide chain of formula (I).

In one embodiment n is 1 in the polypeptide chain of formula (II).

In one embodiment n is 1 in the polypeptide chain of formula (I) and (II).

In one embodiment n is 0 in the polypeptide chain of formula (I) and (II).

Vxx may be derived from a heavy chain variable region, light chain variable region or a combination thereof and may comprise an amino acid linker of 1 to 20 amino acids, for example as described below. In one embodiment Vxx consists of a variable region, in particular a variable region derived from a heavy chain. In one embodiment Vxx represents a light chain variable domain. In one embodiment Vxx is a chimeric variable domain, that is to say it comprises components derived from at least two species, for example a human framework and non-human CDRs. In one embodiment Vxx is humanised.

Vx may be derived from a heavy chain variable region, light chain variable region or a combination thereof, in particular a variable region derived from a heavy chain. In one embodiment Vx represents a light chain variable domain. In one embodiment Vx is a chimeric variable domain, that is to say it comprises components derived from at least two species, for example a human framework and non-human CDRs. In one embodiment Vx is humanised.

Vx in polypeptides of formula (I) corresponds to VH in polypeptide chain (Ia).

VH represents a variable domain, for example a heavy chain variable domain. In one embodiment VH represents a heavy chain variable domain. In one embodiment $V_H$ is a chimeric variable domain, that is to say it comprises components derived from at least two species, for example a human framework and non-human CDRs. In one embodiment VH is humanised.

$V_1$ represents a variable domain, for example a heavy chain or light chain variable domain. In one embodiment $V_1$ represents a heavy chain variable domain. In one embodiment $V_1$ represents a light chain variable domain. In one embodiment $V_1$ is a chimeric variable domain, that is to say it comprises components derived from at least two species, for example a human framework and non-human CDRs. In one embodiment $V_1$ is humanised.

Vyy may be derived from a heavy chain, light chain or a combination thereof and may comprise an amino acid linker of 1 to 20 amino acids, for example as described below. In one embodiment Vyy consists of a variable region, in particular a variable region derived from a light chain. In one embodiment Vyy represents a heavy chain variable domain. In one embodiment Vyy is a chimeric variable domain, that is to say it comprises components derived from at least two species, for example a human framework and non-human CDRs. In one embodiment Vyy is humanised.

Vy may be derived from a heavy chain variable region, light chain variable region or a combination thereof, in particular a variable region derived from a light chain. In one embodiment Vy represents a heavy chain variable domain. In one embodiment Vy is a chimeric variable domain, that is to say it comprises components derived from at least two species, for example a human framework and non-human CDRs. In one embodiment Vy is humanised.

Vy in polypeptides of formula (II) corresponds to VL in polypeptides of formula (IIa).

$V_L$ represents a variable domain, for example a light chain variable domain. In one embodiment $V_L$ represents a light chain variable domain. In one embodiment $V_L$ is a chimeric variable domain, that is to say it comprises components derived from at least two species, for example a human framework and non-human CDRs. In one embodiment $V_L$ is humanised.

$V_2$ represents a variable domain, for example a heavy chain or light chain variable domain. In one embodiment $V_2$ represents a light chain variable domain. In one embodiment $V_2$ represents a heavy chain variable domain. In one embodiment $V_2$ is a chimeric variable domain, that is to say it comprises components derived from at least two species, for example a human framework and non-human CDRs. In one embodiment $V_1$ is humanised.

Generally Vxx and Vyy together form an antigen binding domain. In one embodiment Vxx and Vyy together represent a cognate pair.

Generally Vx and Vy together form an antigen binding domain. In one embodiment Vx and Vy together represent a cognate pair.

In one embodiment the binding domain formed by VH and VL are specific to a first antigen.

In one embodiment VH and VL form a cognate pair.

Generally $V_1$ and $V_2$ together form an antigen binding domain. In one embodiment $V_1$ and $V_2$ together represent a cognate pair.

In one embodiment $V_1$ and $V_2$ together form an antigen binding domain specific for a first antigen (i.e. the two binding domains in the molecule may be specific to the same antigen, for example binding the same or a different epitope therein).

In one embodiment $V_1$ and $V_2$ together are a binding domain for human serum albumin.

In one embodiment $V_1$ and $V_2$ together form an antigen binding domain specific for a second antigen (i.e. the two binding domains in the molecule are specific to different antigens).

In one embodiment the disulfide bond between $V_1$ and $V_2$ is between two of the residues listed below (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA. In one embodiment the disulfide bond is in a position selected from the group comprising:

VH37+VL95C see for example Protein Science 6, 781-788 Zhu et al (1997);

VH44+VL100 see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

VH44+VL105 see for example J Biochem. 118, 825-831 Luo et al (1995);

VH45+VL87 see for example Protein Science 6, 781-788 Zhu et al (1997);

VH55+VL101 see for example FEBS Letters 377 135-139 Young et al (1995);

VH100+VL50 see for example Biochemistry 29 1362-1367 Glockshuber et al (1990);

VH100b+VL49;

VH98+VL 46 see for example Protein Science 6, 781-788 Zhu et al (1997);

VH101+VL46;

VH105+VL43 see for example; Proc. Natl. Acad. Sci. USA Vol. 90 pp. 7538-7542 Brinkmann et al (1993); or Proteins 19, 35-47 Jung et al (1994), VH106+VL57 see for example FEBS Letters 377 135-139 Young et al (1995) and a position corresponding thereto in variable region pair located in the molecule.

The amino acid pairs listed above are in the positions conducive to replacement by cysteines such that disulfide bonds can be formed. Cysteines can be engineered into these desired positions by known techniques. In one embodiment therefore an engineered cysteine according to the present invention refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N.Y., 1989; Ausbel et al., Current Protocols in Molecular Biology, Greene Publishing & Wiley-Interscience, N Y, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

Accordingly in one embodiment a variable domain pair ($V_1/V_2$) of the present invention may be linked by a disulfide bond between two cysteine residues, one in $V_1$ and one in $V_2$, wherein the position of the pair of cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57.

In one embodiment a variable domain pair ($V_1/V_2$) of the present invention may be linked by a disulfide bond between two cysteine residues, one in $V_1$ and one in $V_2$, which are outside of the CDRs wherein the position of the pair of cysteine residues is selected from the group consisting of VH37 and VL95, VH44 and VL100, VH44 and VL105, VH45 and VL87, VH100 and VL50, VH98 and VL46, VH105 and VL43 and VH106 and VL57.

In one embodiment $V_1$ is a heavy chain variable domain and $V_2$ is a light chain variable domain and $V_1$ and $V_2$ are linked by a disulphide bond between two engineered cysteine residues, one at position VH44 of $V_1$ and the other at VL100 of $V_2$.

In one embodiment VH and $V_1$ are variable regions which are both from a heavy chain(s) or a light chain(s), in particular are both derived from two distinct heavy chain variable regions.

In one embodiment VL and $V_2$ are variable regions which are both from a heavy chain(s) or a light chain(s), in particular are both derived from two distinct light chain variable regions.

Cognate pair as employed herein refers to a pair of variable domains from a single antibody, which was generated in vivo, i.e. the naturally occurring pairing of the variable domains isolated from a host. A cognate pair is therefore a VH and VL pair. In one example the cognate pair bind the antigen co-operatively.

Variable region as employed herein refers to the region in an antibody chain comprising the CDRs and a suitable framework.

Variable regions for use in the present disclosure will generally be derived from an antibody, which may be generated by any method known in the art.

Derived from as employed herein refers to the fact that the sequence employed or a sequence highly similar to the sequence employed was obtained from the original genetic material, such as the light or heavy chain of an antibody.

Highly similar as employed herein is intended to refer to an amino acid sequence which over its full length is 95% similar or more, such as 96, 97, 98 or 99% similar.

Antibodies generated against the antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and WO2004/106377.

The antibodies for use in the present invention can also be generated using various phage display methods known in the art and include those disclosed by Brinkman et al. (in J. Immunol Methods, 1995, 182: 41-50), Ames et al. (J. Immunol Methods, 1995, 184:177-186), Kettleborough et al. (Eur. J. Immunol 1994, 24:952-958), Persic et al. (Gene, 1997 187 9-18), Burton et al. (Advances in Immunology, 1994, 57:191-280) and WO90/02809; WO91/10737; WO92/01047; WO92/18619; WO93/11236; WO95/15982; WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; 5,969,108, and WO20011/30305.

In one embodiment the bi-specific molecules according to the disclosure are humanised.

Humanised (which include CDR-grafted antibodies) as employed herein refers to molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

As used herein, the term 'humanised antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a humanised antibody of the present invention, the acceptor heavy and light chains do not necessarily need to be derived from the same antibody and may, if desired, comprise composite chains having framework regions derived from different chains.

The framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

In one embodiment the bi-specific antibodies of the present disclosure are fully human, in particular one or more of the variable domains are fully human.

Fully human molecules are those in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 and EP0463151.

Cx is a constant domain from a light or heavy chain, in particular a heavy chain.

Cx in polypeptide of formula (I) corresponds to $CH_1$ in polypeptides of formula (Ia). In one embodiment Cx is equivalent to $CH_1$.

In one embodiment the $CH_1$ domain is a naturally occurring domain 1 from a heavy chain or a derivative thereof. In one embodiment the CH fragment consists of a $CH_1$ domain.

Cy is a constant domain from a light or heavy chain, in particular a light chain.

Cy in polypeptide of formula (II) corresponds to CL in polypeptides of formula (IIa). In one embodiment Cy is equivalent to CL.

In one embodiment the $C_L$ fragment, in the light chain, is a constant kappa sequence or a constant lambda sequence or a derivative thereof.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

In one embodiment X is a linker for example a suitable peptide for connecting the portions $CH_1$ and $V_1$.

In one embodiment X is a linker for example a suitable peptide for connecting the portions $C_L$ and $V_2$.

In one embodiment the peptide linker is 50 amino acids in length or less, for example 20 amino acids or less.

In one embodiment the linker is selected from a sequence shown in sequence 13 to 77.

In one embodiment the linker is selected from a sequence shown in SEQ ID NO:103 or SEQ ID NO:104.

TABLE 1

Hinge linker sequences

| SEQ ID NO: | SEQUENCE |
|---|---|
| 13 | DKTHTCAA |
| 14 | DKTHTCPPCPA |
| 15 | DKTHTCPPCPATCPPCPA |
| 16 | DKTHTCPPCPATCPPCPATCPPCPA |
| 17 | DKTHTCPPCPAGKPTLYNSLVMSDTAGTCY |
| 18 | DKTHTCPPCPAGKPTHVNVSVVMAEVDGTCY |
| 19 | DKTHTCCVECPPCPA |
| 20 | DKTHTCPRCPEPKSCDTPPPCPRCPA |
| 21 | DKTHTCPSCPA |

TABLE 2

Flexible linker sequences

| SEQ ID NO: | SEQUENCE |
|---|---|
| 22 | SGGGGSE |
| 23 | DKTHTS |
| 24 | (S)GGGGS |
| 25 | (S)GGGGSGGGGS |
| 26 | (S)GGGGSGGGGSGGGGS |
| 27 | (S)GGGGSGGGGSGGGGSGGGGS |
| 28 | (S)GGGGSGGGGSGGGGSGGGGSGGGGS |
| 29 | AAAGSG-GASAS |
| 30 | AAAGSG-XGGGS-GASAS |
| 31 | AAAGSG-XGGGSXGGGS-GASAS |
| 32 | AAAGSG-XGGGSXGGGSXGGGS-GASAS |
| 33 | AAAGSG-XGGGSXGGGSXGGGSXGGGS-GASAS |
| 34 | AAAGSG-XS-GASAS |
| 35 | PGGNRGTTTTRRPATTTGSSPGPTQSHY |
| 36 | ATTTGSSPGPT |
| 37 | ATTTGS |
| — | GS |
| 38 | EPSGPISTINSPPSKESHKSP |
| 39 | GTVAAPSVFIFPPSD |
| 40 | GGGGIAPSMVGGGGS |
| 41 | GGGGKVEGAGGGGS |
| 42 | GGGGSMKSHDGGGGS |
| 43 | GGGGNLITIVGGGGS |
| 44 | GGGGVVPSLPGGGGS |
| 45 | GGEKSIPGGGGS |

TABLE 2-continued

Flexible linker sequences

| SEQ ID NO: | SEQUENCE |
| --- | --- |
| 46 | RPLSYRPPFPFGFPSVRP |
| 47 | YPRSIYIRRRHPSPSLTT |
| 48 | TPSHLSHILPSFGLPTFN |
| 49 | RPVSPFTFPRLSNSWLPA |
| 50 | SPAAHFPRSIPRPGPIRT |
| 51 | APGPSAPSHRSLPSRAFG |
| 52 | PRNSIHFLHPLLVAPLGA |
| 53 | MPSLSGVLQVRYLSPPDL |
| 54 | SPQYPSPLTLTLPPHPSL |
| 55 | NPSLNPPSYLHRAPSRIS |
| 56 | LPWRTSLLPSLPLRRRP |
| 57 | PPLFAKGPVGLLSRSFPP |
| 58 | VPPAPVVSLRSAHARPPY |
| 59 | LRPTPPRVRSYTCCPTP- |
| 60 | PNVAHVLPLLTVPWDNLR |
| 61 | CNPLLPLCARSPAVRTFP |

(S) is optional in sequences 24 to 28.

Examples of rigid linkers include the peptide sequences GAPAPAAPAPA (SEQ ID NO: 62), PPPP (SEQ ID NO: 63) and PPP.

In one embodiment the peptide linker is an albumin binding peptide.

Examples of albumin binding peptides are provided in WO2007/106120 and include:

TABLE 3

| SEQ ID NO: | SEQUENCE |
| --- | --- |
| 64 | DLCLRDWGCLW |
| 65 | DICLPRWGCLW |
| 66 | MEDICLPRWGCLWGD |
| 67 | QRLMEDICLPRWGCLWEDDE |
| 68 | QGLIGDICLPRWGCLWGRSV |
| 69 | QGLIGDICLPRWGCLWGRSVK |
| 70 | EDICLPRWGCLWEDD |
| 71 | RLMEDICLPRWGCLWEDD |
| 72 | MEDICLPRWGCLWEDD |
| 73 | MEDICLPRWGCLWED |
| 74 | RLMEDICLARWGCLWEDD |
| 75 | EVRSFCTRWPAEKSCKPLRG |

TABLE 3-continued

| SEQ ID NO: | SEQUENCE |
| --- | --- |
| 76 | RAPESFVCYWETICFERSEQ |
| 77 | EMCYFPGICWM |

Advantageously use of albumin binding peptides as a linker may increase the half-life of the bi-specific antibody molecule.

For the avoidance of doubt $V_2$ is still present in the antibody molecule and is retained therein by virtue of pairing with $V_1$ including where a disulphide bond is present between $V_1$ and $V_2$.

In one embodiment the bi-specific antibody molecules of the disclosure are capable of selectively binding two different antigens of interest.

In one embodiment, an antigen of interest bound by Vxx/Vyy, Vx/Vy, VH/VL and $V_1/V_2$ are independently selected from a cell-associated protein, for example a cell surface protein on cells such as bacterial cells, yeast cells, T-cells, endothelial cells or tumour cells, and a soluble protein.

Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

Soluble antigens include interleukins such as IL-1, IL-2, IL-3, IL-4, IL-5, IL-6, IL-8, IL-12, IL-16 or IL-17, IL-23, viral antigens for example respiratory syncytial virus or cytomegalovirus antigens, immunoglobulins, such as IgE, interferons such as interferon α, interferon β or interferon γ, tumour necrosis factor-α, tumour necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody fusion protein of the invention may be used to functionally alter the activity of the antigen of interest. For example, the antibody fusion protein may neutralize, antagonize or agonise the activity of said antigen, directly or indirectly.

In one embodiment the antigen of interest bound by VH and VL is OX40. In one embodiment the Vx-Cx or VHCH1 portion of the multi-specific antibody has the sequence given in SEQ ID NO:3. In one embodiment the Vy-Cy or VL-CL portion of the multi-specific antibody has the sequence given in SEQ ID NO:7.

In one embodiment, an antigen of interest bound by VH/VL or $V_1/V_2$ provides the ability to recruit effector functions, such as complement pathway activation and/or effector cell recruitment.

The recruitment of effector function may be direct in that effector function is associated with a cell, said cell bearing a recruitment molecule on its surface. Indirect recruitment may occur when binding of a binding domain (such as $V_1/V_2$) in the molecule according to present disclosure to a recruitment polypeptide causes release of, for example, a factor which in turn may directly or indirectly recruit effector function, or may be via activation of a signalling pathway. Examples include TNFα, IL2, IL6, IL8, IL17, IFNγ, histamine, C1q, opsonin and other members of the classical and alternative complement activation cascades, such as C2, C4, C3-convertase, and C5 to C9.

As used herein, 'a recruitment polypeptide' includes a FcγR such as FcγRI, FcγRII and FcγRIII, a complement pathway protein such as, but without limitation, C1q and C3, a CD marker protein (Cluster of Differentiation marker) such as, but without limitation, CD68, CD115, CD16, CD80, CD83, CD86, CD56, CD64, CD3, CD4, CD8, CD28, CD45, CD19, CD20 and CD22. Further recruitment polypeptides which are CD marker proteins include CD1, CD1d, CD2, CD5, CD8, CD9, CD10, CD11, CD11a, CD11b, CD11c, CD13, CD14, CD15, CD16, CD18, CD19, CD20, CD21, CD22, CD23, CD24, CD25, CD26, CD27, CD28, CD29, CD30, CD31, CD32, CD33, CD34, CD35, CD36, CD37, CD38, CD40, CD43, CD44, CD45, CD46, CD49, CD49a, CD49b, CD49c, CD49d, CD52, CD53, CD54, CD55, CD56, CD58, CD59, CD61, CD62, D62E, CD62L, CD62P, CD63, CD64, CD66e, CD68, CD70, CD71, CD72, CD79, CD80, CD81, CD82, CD83, CD84, CD85, CD86, CD88, CD89, CD90, CD94, CD95, CD98, CD106, CD114, CD116, CD117, CD118, CD120, CD122, CD130, CD131, CD132, CD133, CD134, CD135, CD137, CD138, CD141, CD142, CD143, CD146, CD147, CD151, CD152, CD153, CD154, CD155, CD162, CD164, CD169, CD184, CD206, CD209, CD257, CD278, CD281, CD282, CD283 and CD304, or a fragment of any thereof which retains the ability to recruit cell-mediated effector function either directly or indirectly. A recruitment polypeptide also includes immunoglobulin molecules such as IgG1, IgG2, IgG3, IgG4, IgE and IgA which possess effector function.

In one embodiment, a binding domain (such as $V_1/V_2$) in the molecule according to the present disclosure has specificity is a complement pathway protein, with C1q being particularly preferred.

Further, molecules of the present invention may be used to chelate radionuclides by virtue of a single domain antibody which binds to a nuclide chelator protein. Such fusion proteins are of use in imaging or radionuclide targeting approaches to therapy.

In one embodiment, one binding domain in a molecule according to the disclosure (such as $V_1/V_2$) has specificity is a CD marker protein, with CD68, CD80, CD86, CD64, CD3, CD4, CD8 CD45, CD16 and CD35 being particularly preferred.

In one embodiment a binding domain within a molecule according to the disclosure (such as $V_1/V_2$) has specificity for a serum carrier protein, a circulating immunoglobulin molecule, or CD35/CR1, for example for providing an extended half-life to the antibody fragment with specificity for said antigen of interest by binding to said serum carrier protein, circulating immunoglobulin molecule or CD35/CR1.

As used herein, 'serum carrier proteins' include thyroxine-binding protein, transthyretin, α1-acid glycoprotein, transferrin, fibrinogen and albumin, or a fragment of any thereof.

As used herein, a 'circulating immunoglobulin molecule' includes IgG1, IgG2, IgG3, IgG4, sIgA, IgM and IgD, or a fragment of any thereof.

CD35/CR1 is a protein present on red blood cells which have a half-life of 36 days (normal range of 28 to 47 days; Lanaro et al., 1971, Cancer, 28(3):658-661).

In one embodiment, the protein for which $V_1/V_2$ has specificity is a serum carrier protein, such as a human serum carrier. In a most preferred embodiment, the serum carrier protein is human serum albumin.

Albumin binding variable regions and CDRs are disclosed in constructs shown in FIG. 1.

Thus in one embodiment there is provided a bi-specific antibody molecule comprising or consisting of three polypeptides;

a) a heavy chain of formula (Ia):

$VH-CH_1-X-V_1$; and b) a light chain of formula (IIa):

$VL-C_L$ c) a polypeptide of formula (III):

$V_2$ wherein
$V_H$ represents a heavy chain variable domain,
$CH_1$ represents domain 1 of a heavy chain constant region,
X represents a linker,
$V_1$ represents a variable domain,
$V_L$ represents a light chain variable domain,
$C_L$ represents a constant region from a light chain,
$V_2$ represents a variable region,
wherein $V_H$ and $V_L$ are a cognate pair of variable regions aligned to form a binding domain and $V_1$ and $V_2$ are a cognate pair of variable regions aligned to form a binding domain optionally a disulphide bond therebetween, for example wherein $V_1$ and $V_2$ are capable of binding albumin in vivo, in particular human serum albumin.

In one embodiment V1 or V2 comprise a sequence selected from the group consisting of SEQ ID NO:4, SEQ ID NO:8, SEQ ID NO:83 and SEQ ID NO:86. In one embodiment V1 has the sequence given in SEQ ID NO:4 and V2 has the sequence given in SEQ ID NO:8. In one embodiment V1 has the sequence given in SEQ ID NO:86 and V2 has the sequence given in SEQ ID NO:83.

In one example V1 or V2, in particular V1, is a VH domain comprising the sequence given in SEQ ID NO:87 for CDRH-1, the sequence given in SEQ ID NO:88 for CDRH2 and the sequence given in SEQ ID NO:89 for CDRH-3. In one example V1 or V2, in particular V1, is a VH domain comprising the sequence given in SEQ ID NO:93 for CDRH-1, the sequence given in SEQ ID NO:94 for CDRH2 and the sequence given in SEQ ID NO:95 for CDRH-3.

In one embodiment V1 or V2, in particular V2, is a VL domain comprising the sequence given in SEQ ID NO:90 for CDRL-1, the sequence given in SEQ ID NO:91 for CDRL2 and the sequence given in SEQ ID NO:92 for CDRL-3. In one embodiment V1 or V2, in particular V2, is a VL domain comprising the sequence given in SEQ ID NO:96 for CDRL-1, the sequence given in SEQ ID NO:97 for CDRL2 and the sequence given in SEQ ID NO:98 for CDRL-3.

In one example V1 or V2, in particular V1, is a VH domain comprising the sequence given in SEQ ID NO:4, SEQ ID NO: 86, SEQ NO:99 or SEQ ID NO:100.

In one example V1 or V2, in particular V2, is a VL domain comprising the sequence given in SEQ ID NO: 8, SEQ ID NO: 83, SEQ NO:101 or SEQ ID NO:102.

In one example V1 is a VH domain comprising the sequence given in SEQ NO:99 and V2 is a VL domain comprising the sequence given in SEQ NO:101.

In one example V1 is a VH domain comprising the sequence given in SEQ NO:100 and V2 is a VL domain comprising the sequence given in SEQ NO:102.

In one example polypeptide Ia has the sequence given in SEQ ID NO:6.

In one example polypeptide IIa has the sequence given in SEQ ID NO:7.

In one example polypeptide Ib has the sequence given in SEQ ID NO:3.

In one example polypeptide IIb has the sequence given in SEQ ID NO:5.

In one example polypeptide Ia has the sequence given in SEQ ID NO:6, polypeptide IIa has the sequence given in SEQ ID NO:7 and $V_2$ has the sequence given in SEQ ID NO:8.

In one example polypeptide Ib has the sequence given in SEQ ID NO:3, polypeptide IIb has the sequence given in SEQ ID NO:5 and $V_1$ has the sequence given in SEQ ID NO:4.

The invention also provides sequences which are 80%, 90%, 91%, 92%, 93% 94%, 95% 96%, 97%, 98% or 99% similar to a sequence or antibody disclosed herein.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In an alternative aspect the present invention provides a Fab or Fab' fragment linked to a disulphide stabilised scFv, wherein the disulphide stabilised scFv (dsscFv) is linked to the C-terminus of the heavy or the light chain of the Fab or Fab' fragment directly or via a linker such as a linker described herein. Preferably the Fab-dsscFv fusion protein is bi-specific. In one example the dsscFv binds a serum carrier protein such as human serum albumin. In one example the dsscFv is linked to C-terminus of the heavy chain of the Fab or Fab' fragment by the linker given in SEQ ID NO:78. In one example the dsscFv is linked to the C-terminus of the light chain of the Fab or Fab' fragment by the linker given in SEQ ID NO:103. In one example the heavy chain of the Fab-dsscFv has the sequence given in SEQ ID NO:9 and the light chain has the sequence given in SEQ ID NO:10. In one example the heavy chain of the Fab-dsscFv has the sequence given in SEQ ID NO:11 and the light chain has the sequence given in SEQ ID NO:12.

In one embodiment the bi-specific antibody molecules of the present disclosure are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

Improved affinity as employed herein in this context refers to an improvement over the starting molecule.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof. "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, a Fab or Fab' in the molecule is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido)propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

$H_3CO-(CH_2CH_2O)_n$
$H_3CO-(CH_2CH_2O)_n$-O-CH_2CH_2CH_2-NH-C(O)-(CH_2)_m-N(maleimide)

m is 2 or 5

That is to say each PEG is about 20,000 Da.
Further alternative PEG effector molecules of the following type:

$CH_3O-(CH_2CH_2O)_n$
$CH_3O-(CH_2CH_2O)_n$-phenyl-CH_2CH_2-N(maleimide)

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering).

In one embodiment there is provided a polynucleotide sequence encoding a molecule of the present disclosure, such as a DNA sequence.

In one embodiment there is provided a polynucleotide sequence encoding one or more, such as two or more polypeptide components of a molecule of the present disclosure, for example a polypeptide chain of formula (I):

$(Vxx)_n Vx\text{-}Cx\text{-}X\text{-}V_1$ a polypeptide chain of formula (II):

$(Vyy)_n Vy\text{-}Cy$ or a polypeptide of formula (III):

$V_2$ wherein
Vx represents a variable domain,
Vxx represents a variable domain,
Cx represents a constant region domain,
X represents a linker,
$V_1$ represents a variable domain,
Vy represents a variable domain,
Vyy represents a variable domain,
Cy represents a constant region domain,
$V_2$ represents a variable domain,
n independently represents 0 or 1.

In one embodiment the polynucleotide, such as the DNA is comprised in a vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides. In one example the cell line may be transfected with three vectors, each encoding a polypeptide chain of an antibody molecule of the present invention. In one example the cell line is transfected with three vectors each one encoding a different polypeptide selected from a) a polypeptide chain of formula (I):

$(Vxx)_n Vx\text{-}Cx\text{-}X\text{-}V_1;$ b) a polypeptide chain of formula (II):

$(Vyy)_n Vy\text{-}Cy$ and c) a polypeptide of formula (III):

$V_2$ wherein
Vx represents a variable domain,
Vxx represents a variable domain,
Cx represents a constant region domain,
X represents a linker,
$V_1$ represents a variable domain,
Vy represents a variable domain,
Vyy represents a variable domain,
Cy represents a constant region domain,
$V_2$ represents a variable domain,
n independently represents 0 or 1, It will be appreciated that the ratio of each vector transfected into the host cell may be varied in order to optimise expression of the multi-specific antibody product. In one embodiment the ratio of vectors is 1:1:1. It will be appreciated that skilled person is able to find an optimal ratio by routine testing of protein expression levels following transfection.

It will also be appreciated that where two or more, in particular three of more, of the polypeptide components are encoded by a polynucleotide in a single vector the relative expression of each polypeptide component can be varied by utilising different promoters for each polynucleotide encoding a polypeptide component of the present invention.

In one embodiment the vector comprises a single polynucleotide sequence encoding all three polypeptide chains of the multispecific antibody molecule of the present invention under the control of a single promoter.

In one embodiment the vector comprises a single polynucleotide sequence encoding all three polypeptide chains of the multispecific antibody molecule of the present invention wherein each polynucleotide sequence encoding each polypeptide chain is under the control of a different promoter.

The antibodies and fragments according to the present disclosure are expressed at good levels from host cells. Thus the properties of the antibodies and/or fragments appear to be optimised and conducive to commercial processing.

The antibodies of the present invention are useful in the treatment and/or prophylaxis of a pathological condition.

The present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for use in treatment and for the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody, fragment or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternatively a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

In one embodiment, in formulations according to the present disclosure, the pH of the final formulation is not similar to the value of the isoelectric point of the antibody or fragment, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared. Preferably the antibody molecules of the present invention are administered subcutaneously, by inhalation or topically.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases (such as nebulisable solutions or suspensions). Inhalable powders according to the disclosure containing the active substance may consist solely of the abovementioned active substances or of a mixture of the above mentioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active (such as the antibody or fragment is of primary importance).

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

In one embodiment the formulation is provided as discrete ampoules containing a unit dose for delivery by nebulisation.

In one embodiment the antibody is supplied in lyophilised form, for reconstitutions or alternatively as a suspension formulation.

The antibody of the invention can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The antibodies of the present disclosure are thought to be suitable for delivery via nebulisation. It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia.

The present invention also provides an antibody molecule according to the present invention for use in the treatment or prophylaxis of pain, particularly pain associated with inflammation.

Thus there is provided an antibody according to the invention for use in treatment and methods of treatment employing same.

In one embodiment there is provided a process for purifying an antibody (in particular an antibody or fragment according to the invention).

In one embodiment there is provided a process for purifying an antibody (in particular an antibody or fragment according to the invention) comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

The antibody molecule of the present invention may also be used in diagnosis, for example in the in vivo diagnosis and imaging of disease states involving OX40.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

EXAMPLES

Example 1: Single Linker Fab-dsFv

Construction of Single Linker A26Fab-645dsFv, A26Fab-645dsFv and A26Fab-645dsscFv Plasmids for Expression in Mammalian Cells A26Fab fusion proteins for the expression of single linker A26Fab-645dsFv and A26Fab-645dsFv, see FIG. 1, were constructed by fusing 645vL to the C-terminus of the Km3 allotype human kappa constant region of the A26 light chain using the flexible linker SGGGGSGGGGSGGGGS (SEQ ID NO: 103), or by fusing 645vH to the C-terminus of the, γ1 isotype human gamma-1 CH1 constant region of the A26 heavy chain using the flexible linker SGGGGSGGGGTGGGGS (SEQ ID NO: 78). In addition point mutations were introduced into the DNA sequences at selected residues in the framework region of both 645vL and 645vH. The mutations (heavy chain G44C and light chain G100C) were introduced to create an interchain disulphide bond between the heavy and light chains of the 645Fv. A26Fab fusion proteins for the expression of A26Fab-645dsscFv, see FIG. 1, were constructed as follows. A single chain Fv (scFv) was constructed by linking the N-terminus of 645vL to the C-terminus of 645vH via the flexible linker GGGGSGGGGSGGGGSGGGGS (SEQ ID NO: 79). Point mutations were introduced into the DNA sequence at framework residues G100C in 645vL and G44C in 645vH to make the disulphide linked scFv (dsscFv). The 645dsscFv was then fused to the C-terminus of either the Km3 allotype human kappa constant region of the A26 light chain using the flexible linker SGGGGSGGGGS (SEQ ID NO: 104), or to the γ1 isotype human gamma-1 CH1 constant region of the A26 heavy chain using the flexible linker SGGGGTGGGGS (SEQ ID NO: 80). The A26Fab light chain-645dsvL, A26Fab heavy chain-645dsvH, A26Fab light chain, A26Fab heavy chain, 645dsvL free domain, 645dsvH free domain, A26Fab light chain-645dsscFv and A26Fab heavy chain-645dsscFv were manufactured chemically and individually cloned into mammalian expression vectors under the control of the HCMV-MIE promoter and SV40E polyA sequence.

HEK293 Expression of Single Linker A26Fab-645dsFv, A26Fab-645dsFv and A26Fab-645dsscFv HEK293 cells were transfected with the relevant plasmids using Invitrogen's 293fectin transfection reagent according to the manufacturer's instructions. Plasmids were mixed as follows to express the different constructs; for A26Fab-645dsFv, the plasmids were A26Fab Heavy-(S, 3×G4S/T)-645dsvH and A26Fab Light-(S, 3×G4S)-645dsvL; for Single linker A26Fab-645dsFv (LC-vL linked), the plasmids were A26Fab Heavy, 645dsvH and A26Fab Light-(S, 3×G4S)-645dsvL; for Single linker A26Fab-645dsFv (HC-vH linked), the plasmids were A26Fab Heavy-(S, 3×G4S/T)-645dsvH, A26Fab Light and 645dsvL; for A26Fab-645dsscFv (HC-scFv), the plasmids were A26Fab Heavy-(S, 2×G4S/T)-645dsscFv(vH-4×G4S-vL) and A26Fab Light; and for A26Fab-645dsscFv (LC-scFv), the plasmids were A26Fab Heavy and A26Fab Light-(S, 2×G4S)-645dsscFv (vH-4×G4S-vL). In addition the ratio of the plasmids used for the transfections also varied, for the 2 plasmid combinations the ratio was 1:1, whereas for the 3 plasmid combinations several different ratios were tested. A total of 50 μg of plasmid DNA was incubated with 125 μl 293 fectin+4.25 ml Optimem media for 20 mins at RT. The mixture was then added to 50 ml of HEK293 cells in suspension at 1×10⁶ cells/ml and incubated with shaking at 37° C. Supernatants were harvested on day 7 by centrifugation at 1500 g to remove cells and the supernatant passed through a 0.22 μm filter. Expression level was determined by Protein-G HPLC.

The level of expression of all the constructs was comparable, see table 4, covering the range 3-15 μg/ml. The Fab-dsFv expressed at 13-14 μg/ml, the Fab-dsscFv's expressed at 7-15 μg/ml and the single linker Fab-dsFv's expressed at 3-13 μg/ml. There have been reports in the literature that the expression of Fv regions that lack either a linker between the vL and vH or a dimerisation motif to bring the vL and vH together have substantially lower expression levels than linked Fv's. This is not observed in this data where there is no significant difference observed between the best expression of each type of construct.

TABLE 4

| Construct | Expression level (μg/ml) |
| --- | --- |
| A26Fab-645dsFv | 13.2-14.2 |
| A26Fab-645dsscFv (LC-scFv) | 14.0-15.2 |

TABLE 4-continued

| Construct | Expression level (μg/ml) |
| --- | --- |
| A26Fab-645dsscFv (HC-scFv) | 6.6-7.1 |
| single linker A26Fab-645dsFv (LC-vL linked) (ratio 1:1:1 LC-vL:HC:vH) | 5.1-6.9 |
| single linker A26Fab-645dsFv (LC-vL linked) (ratio 1:1:2 LC-vL:HC:vH) | 3.3-3.5 |
| single linker A26Fab-645dsFv (LC-vL linked) (ratio 2:1:2 LC-vL:HC:vH) | 4.2-4.4 |
| single linker A26Fab-645dsFv (LC-vL linked) (ratio 1:2:2 LC-vL:HC:vH) | 4.2-4.3 |
| single linker A26Fab-645dsFv (HC-vH linked) (ratio 1:1:1 HC-vH:LC:vL) | 6.8-12.6 |
| single linker A26Fab-645dsFv (HC-vH linked) (ratio 1:1:2 HC-vH:LC:vL) | 7.8-8.1 |
| single linker A26Fab-645dsFv (HC-vH linked) (ratio 2:1:2 HC-vH:LC:vL) | 7.6-8.2 |

BIAcore Analysis of HEK293 Expressed Single Linker A26Fab-645dsFv, A26Fab-645dsFv and A26Fab-645dsscFv Binding affinities and kinetic parameters for the interactions of Fab-dsFv, Fab-dsscFv and single linker Fab-dsFv constructs were determined by surface plasmon resonance (SPR) conducted on a BIAcore T100 using CM5 sensor chips and HBS-EP (10 mM HEPES (pH7.4), 150 mM NaCl, 3 mM EDTA, 0.05% v/v surfactant P20) running buffer. Single linker Fab-dsFv samples were captured to the sensor chip surface using either a human F(ab')₂-specific goat Fab (Jackson ImmunoResearch, 109-006-097) or an in-house generated anti human CH1 monoclonal antibody. Covalent immobilisation of the capture antibody was achieved by standard amine coupling chemistry.

Each assay cycle consisted of firstly capturing the Fab-dsFv, Fab-dsscFv or single linker Fab-dsFv construct using a 1 min injection, before an association phase consisting of a 3 min injection of antigen, after which dissociation was monitored for 5 min. After each cycle, the capture surface was regenerated with 2×1 min injections of 40 mM HCl followed by 30 s of 5 mM NaOH. The flow rates used were 100 min for capture, 30 μl/min for association and dissociation phases, and 100 min for regeneration.

For kinetic assays, either a titration of human serum albumin 50-6.25 nM, or a single concentration of OX40 of 25 nM was performed. A blank flow-cell was used for reference subtraction and buffer-blank injections were included to subtract instrument noise and drift.

Kinetic parameters were determined by simultaneous global-fitting of the resulting sensorgrams to a standard 1:1 binding model using BIAcore T100 Evaluation software.

The on rates, off rates and affinities of all the samples are similar for both antigens, human serum albumin (HSA) and human OX40, see table 5. Therefore the presence and position of the different linkers in the different constructs does not have a significant effect on the affinity of either variable region for its antigen.

TABLE 5

| Sample | Antigen | ka (1/Ms) | kd (1/s) | KD (nM) | Antigen | ka (1/Ms) | kd (1/s) | KD (pM) |
| --- | --- | --- | --- | --- | --- | --- | --- | --- |
| A26Fab-645dsFv (start) | HSA | 7.51E+04 | 1.51E−04 | 2.01 | OX40 | 1.70E+05 | 1.53E−05 | 90 |
| A26Fab-645dsscFv (HC-scFv) | HSA | 1.83E+05 | 2.40E−04 | 1.31 | OX40 | 1.66E+05 | 2.34E−05 | 141 |
| A26Fab-645dsscFv (LC-scFv) | HSA | 1.72E+05 | 2.22E−04 | 1.29 | OX40 | 1.78E+05 | 1.82E−05 | 102 |

TABLE 5-continued

| Sample | Antigen | ka (1/Ms) | kd (1/s) | KD (nM) | Antigen | ka (1/Ms) | kd (1/s) | KD (pM) |
|---|---|---|---|---|---|---|---|---|
| Single linker A26Fab-645dsFy (LC-vL) (ratio 1:1:1 LC-vL:HC:vH) | HSA | 7.40E+04 | 2.35E−04 | 3.17 | OX40 | 2.29E+05 | 2.64E−05 | 115 |
| Single linker A26Fab-645dsFy (LC-vL) (ratio 1:1:2 LC-vL:HC:vH) | HSA | 1.13E+05 | 2.62E−04 | 2.31 | OX40 | 1.84E+05 | 1.80E−05 | 98 |
| Single linker A26Fab-645dsFy (LC-vL) (ratio 2:1:2 LC-vL:HC:vH) | HSA | 1.26E+05 | 1.88E−04 | 1.49 | OX40 | 1.70E+05 | 1.69E−05 | 99 |
| Single linker A26Fab-645dsFy (LC-vL) (ratio 1:1:1 LC-vL:HC:vH) | HSA | 9.10E+04 | 2.23E−04 | 2.46 | OX40 | 1.54E+05 | 1.70E−05 | 110 |
| Single linker A26Fab-645dsFy (HC-vH) (Ratio 1:1:1 HC-vH:LC:vL) | HSA | 2.09E+05 | 2.09E−04 | 1.00 | OX40 | 1.73E+05 | 3.51E−05 | 203 |
| Single linker A26Fab-645dsFy (HC-vH) (Ratio 1:1:2 HC-vH:LC:vL) | HSA | 2.11E+05 | 2.34E−04 | 1.11 | OX40 | 1.92E+05 | 1.00E−05 | 52 |
| Single linker A26Fab-645dsFy (HC-vH) (Ratio 2:1:2 HC-vH:LC:vL) | HSA | 1.97E+05 | 2.07E−04 | 1.05 | OX40 | 1.94E+05 | 1.97E−05 | 101 |
| A26Fab-645dsFy (end) | HSA | 6.82E+04 | 2.12E−04 | 3.11 | OX40 | 1.93E+05 | 1.98E−05 | 102 |

Protein-G Purification of HEK293 Expressed Single Linker A26Fab-645dsFv, A26Fab-645dsFv and A26Fab-645dsscFv The ~50 ml HEK293 supernatants were concentrated ~25 fold to ~2 ml using 10 kDa molecular weight cut off centrifugation concentrators. The concentrated supernatants were applied to a 1 ml HiTrap Protein-G FF column (GE Healthcare) equilibrated in 20 mM phosphate, 40 mM NaCl pH7.4. The column was washed with 20 mM phosphate, 40 mM NaCl pH7.4 and the bound material eluted with 0.1M glycine/HCl pH2.7. The elution peak was collected and pH adjusted to ~pH7 with 2M Tris/HCl pH8.5. The pH adjusted elutions were concentrated and buffer exchanged into PBS pH7.4 using 10 kDa molecular weight cut off centrifugation concentrators.

SDS-PAGE Analysis of Protein-G Purified, HEK293 Expressed, Single Linker A26Fab-645dsFv, A26Fab-645dsFv and A26Fab-645dsscFv Samples were diluted with water where required and then to 26 µl was added 10 µL 4×Bis-Tris LDS sample buffer and 4 µL of 10× reducing agent for reduced samples. The samples were vortex mixed, incubated at 100° C. for 3 minutes, cooled and centrifuged at 12500 rpm for 30 seconds. The prepared samples were loaded on to a 4-20% acrylamine Tris/Glycine SDS gel and run for 110 minutes at 125V, constant voltage. The gels were stained with Coomassie Blue protein stain, see FIG. 2.

The reducing SDS-PAGE gel has banding patterns in terms of both migration position and staining intensity that is constant with all the constructs being expressed correctly. For Fab-dsFv, lane 2, there should be 2 bands at ~36 and ~37 kDa with roughly equivalent staining. For Fab-dsscFv (LC-scFv), lane 3, there should be 2 bands at ~51 and ~23 kDa with roughly twice the staining in the upper band. For Fab-dsscFv (HC-scFv), lane 4, there should be 2 bands at ~50 and ~26 kDa with roughly twice the staining in the upper band. For single linker Fab-dsFv (LC-vL), lanes 6-9, there should be 3 bands at ~36, ~23 and ~13 kDa with staining roughly in the ratio 3:2:1 upper to lower band. For single linker Fab-dsFv (HC-vH), lanes 10-12, there should be 3 bands at ~37, ~26 and ~12 kDa with staining roughly in the ratio 3:2:1 upper to lower band.

G3000 SEC-HPLC Analysis of Protein-G Purified, HEK293 Expressed, Single Linker A26Fab-645dsFv, A26Fab-645dsFv and A26Fab-645dsscFv 50 µg samples were injected onto a TSK Gel G3000SWXL, 7.8×300 mm, column (Tosoh) and developed with an isocratic gradient of 200 mM phosphate pH7.0 at 1 ml/min. Signal detection was by absorbance at 280 nm, see FIG. 3. After Protein-G purification A26Fab-645dsFv is ~45% monomer, A26Fab-645dsscFv's have slightly more monomer in the range 55-60%, whereas the single linker A26Fab-645dsFv's are all in excess of 80% monomer with some being 100% monomer.

Example 2

Construction of Single Linker A26Fab-645dsFv and A26Fab-648dsFv Triple Gene Plasmids for Expression in Mammalian Cells The triple gene plasmids were constructed by first generating an intermediate double gene vector from the single gene components of the single linker Fab-dsFv formats as described in example 1/FIG. 1. The gene fragment encoding the expression of the heavy chain which includes the hCMV-MIE promoter, the heavy chain and SV40 polyA region, was sub-cloned downstream of the light chain gene in a mammalian expression vector. The heavy chain is either a A26 Fab heavy chain or the A26 Fab heavy linked to a 645dsvH or 648dsvH via a linker (S, 3×G$_4$S), and the light chain is either a A26 Fab light linked to a 645dsvL or 648dsvL via a linker (S, 3×G$_4$S) or a A26 Fab light chain, respectively. This generated the intermediate double gene plasmid for each format. To construct the triple gene plasmid, the gene fragment encoding the expression of the free cognate v region (645dsvL, 648dsvL, 645dsvH or 648dsvH), was subsequently sub-cloned at a unique restriction site downstream of the heavy chain gene in the intermediate vector. For future stable cell line generation, a mammalian selection marker was finally sub-cloned into the expression plasmids. This provided a set of plasmids that contained the relevant genes for single linker Fab-dsFv expression at equal gene ratios, with or without a mammalian selection marker. These plasmids will be used for initial assessment in a transient mammalian expression system for comparison with % monomer (FIG. 3) of single linker Fab-dsFvs expressed from single gene plasmids.

Transient Expression of Single Linker A26Fab-645dsFv and A26Fab-648dsFv from Triple Gene Plasmids in CHO Cells CHO cells were grown in CD CHO media supplemented with 1× L-glutaMAX (Life Technologies) to exponential phase with >99% viability. The cells were prepared by washing in Earle's balanced salt solution (Life Technologies) and plasmid DNA was electroporated into the CHO cells according to in-house recommendations. The transfected cells were transferred to CD CHO medium supplemented with 1× L-glutaMAX and 1× anti-mycotic solution (Life Technologies) and incubated in an orbital shaker for 24 h at 37° C., 8% $CO_2$, and shaking at 140 rpm. Following incubation, or when the cultures had reached a viable cell density of at least $2 \times 10^6$ cells $ml^{-1}$, the temperature was decreased to 32° C. Subsequently after 72 h post-transfection, 3 mM sodium butyrate (Sigma Aldrich) was added and the cultures were re-incubated for a further 11 days at 32° C., with 8% $CO_2$ and shaking at 140 rpm. The supernatant was harvested by centrifugation and successively filtered through 0.45 μM and 0.22 μM sterile filters. Expression titres were quantified by protein G HPLC against a Fab fragment standard.

The level of expression from triple gene plasmids was dependent on the presence of the mammalian selection marker, see FIG. 5. Expression titres were higher amongst single linker A26 Fab-dsFv proteins expressed from plasmids without a mammalian selection marker whereas lower but comparable levels were obtained if expressed from plasmids with the mammalian selection marker, as would be expected due to the metabolic burden exacted by expression of an extra gene. Additionally, higher expression titres were observed for proteins that contained an A26 Fab light linked to a 645dsvL or 648dsvL chain.

Protein G Purification of Single Linker A26Fab-645dsFv and A26Fab-648dsFv Expressed from Triple Gene Plasmids in CHO Cells The 200 ml supernatants were concentrated by ~20-fold using a 10 kDa molecular weight cut off centrifugation concentrators. The concentrated supernatants were applied to a 1 ml HiTrap Protein-G FF column (GE Healthcare) equilibrated in 20 mM phosphate, 40 mM NaCl pH7.4. The column was washed with 20 mM phosphate, 40 mM NaCl pH7.4 and the bound material eluted with 0.1M glycine/HCl pH2.7. The elution peak was collected and the pH adjusted to ~pH7 with Tris/HCl pH8.5. The pH adjusted elutions were concentrated and buffer exchanged into PBS pH7.4 using 10 kDa molecular weight cut off centrifugation concentrators. Protein concentrations were estimated spectrophotometrically at $A_{280}$.

SDS-PAGE Analysis of Protein-G Purified Single Linker A26Fab-645dsFv and A26Fab-648dsFv Expressed from Triple Gene Plasmids in CHO Cells Protein samples were diluted in PBS where required. To 8.25 μl of the subsequent sample, 3.75 μl of 4×Bis-Tris LDS sample buffer (Life Technologies), 1.5 μl of 100 mM N-ethylmaleimide and 1.5 μl of 10× reducing agent were added for reduced samples. The samples were vortex mixed, incubated at 100° C. for 3 minutes, cooled and centrifuged at 13200 rpm for 30 seconds. The prepared samples were loaded on to a 4-20% acrylamide Tris/Glycine SDS gel (Life Technologies) and run in Tris-glycine buffer for ~150 minutes at 125V, constant voltage. An SDS-PAGE protein standard, Seeblue2 (Life Technologies) was used as the standard marker. The gels were stained with InstantBlue Coomassie blue protein stain (Expedeon) and destained with distilled water, see FIG. 6.

The reducing SDS-PAGE gel has banding patterns in terms of both migration position and staining intensity that is constant with all the constructs being expressed correctly. For all single linker Fab-dsFv there should be 3 bands at ~36-37 (i), ~24-26 (ii) and ~12-13 kDa (iii), with staining should be roughly in the ratio of 3:2:1 upper to lower band.

G3000 SEC-HPLC of Protein-G Purified Single Linker A26Fab-645dsFv and A26Fab-648dsFv Expressed from Triple Gene Plasmids in CHO Cells 50 ul samples were injected into a TSK Gel G3000SWXL, 7.8×300 mm, column (Tosoh) and developed with an isocratic gradient of 200 mM phosphate pH7.0 at 1 ml/min. Signal detection was by absorbance at 280 nm, see FIG. 7. All single linker A26Fab-645dsFvs expressed from triple gene plasmids, irrespective of the presence of a mammalian selection marker or expression level, achieve in excess of 90% monomer, with the majority being 100% monomer. This data is in good agreement with the monomeric single linker A26Fab-dsFvs expressed from single gene plasmids, FIG. 3. This also indicates that an equal gene ratio of the relevant genes encoding the format, as present in a triple gene plasmid configuration is optimal for highly monomeric single linker Fab-dsFv expression.

The invention claimed is:

1. A pharmaceutical composition comprising a purified monomeric form of a multi-specific antibody molecule and at least one excipient, said multi-specific antibody molecule consisting of three polypeptides, a) a polypeptide chain of formula (I):

(Vxx)ₙVx-Cx-X-V₁, b) a polypeptide chain of formula (II):

(Vyy)ₙVy-Cy, and c) a polypeptide of formula (III):

V₂, wherein

Vx represents a variable domain,

Vxx represents a variable domain,

Cx represents a constant region consisting of $CH_1$,

X represents a linker,

V₁ represents a variable domain,

Vy represents a variable domain,

Vyy represents a variable domain,

Cy represents a constant region selected from a Ckappa or Clambda sequence,

V₂ represents a variable domain, n independently represents 0 or 1, wherein the polypeptide chain of formula (I) and the polypeptide chain of formula (II) is aligned such that the constant regions Cx and Cy are paired, the variable domains Vx and Vy are paired to form a binding domain, the variable domains V₁ and V₂ are paired to form a binding domain, and a disulphide bond is present between V₁ and V₂, and wherein at least 90 percent of the antibody molecules in the composition are in monomeric form;

wherein the variable domain pair V₁/V₂ are linked by a disulfide bond between two engineered cysteine residues, one in V₁ and one in V₂; and wherein the position of the pair of engineered cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57.

2. The pharmaceutical composition of claim 1, wherein a) in the polypeptide chain of formula (I), (Vxx)nVx is $V_H$, b) in the polypeptide chain of formula (II), (Vyy)nVy is $V_L$ and $C_y$ is $C_L$, $V_H$ represents a heavy chain variable domain, $V_L$ represents a light chain variable domain, $C_L$ represents a constant region from a light chain.

3. The pharmaceutical composition according to claim 1, wherein V₁ represents a heavy chain variable domain and V₂ represents a light chain variable domain.

4. The pharmaceutical composition according to claim 1 wherein the variable domain pair V₁/V₂ have specificity for a serum carrier protein.

5. The pharmaceutical composition according to claim 4 wherein V₁ comprises the sequence given in SEQ ID NO:87 for CDRH-1, the sequence given in SEQ ID NO:88 for CDRH2 and the sequence given in SEQ ID NO:89 for CDRH-3 and V2 comprises the sequence given in SEQ ID NO:90 for CDRL-1, the sequence given in SEQ ID NO:91 for CDRL2 and the sequence given in SEQ ID NO:92 for CDRL-3.

6. The pharmaceutical composition according to claim 4 wherein V₁ comprises the sequence given in SEQ ID NO:93 for CDRH-1, the sequence given in SEQ ID NO:94 for CDRH2 and the sequence given in SEQ ID NO:95 for CDRH-3 and V2 comprises the sequence given in SEQ ID NO:96 for CDRL-1, the sequence given in SEQ ID NO:97 for CDRL2 and the sequence given in SEQ ID NO:98 for CDRL-3.

7. The pharmaceutical composition according to claim 1 wherein X has the sequence given in SEQ ID NO:78.

8. The pharmaceutical composition according to claim 1, wherein a natural disulfide bond is present between Cx and Cy.

9. The pharmaceutical composition according to claim 1, wherein at least one binding domain of the multi-specific antibody molecule is specific for an antigen selected from the group consisting of an immunoglobulin, an interferon, a colony stimulating factor, a viral antigen, a member of the classical and alternative complement activation cascade, an FcγR, a complement pathway protein, an integrin, and an interleukin.

10. The pharmaceutical composition according to claim 9, wherein the at least one binding domain is specific for IgE.

11. The pharmaceutical composition according to claim 9, wherein the at least one binding domain is specific for an interferon selected from the group consisting of interferon α, interferon β, and interferon γ.

12. The pharmaceutical composition according to claim 9, wherein the at least one binding domain is specific for a colony stimulating factor selected from the group consisting of G-CSF and GM-CSF.

13. The pharmaceutical composition according to claim 9, wherein the at least one binding domain is specific for a viral antigen selected from the group consisting of a respiratory syncytial virus or cytomegalovirus, influenza, EBV, HepA, B and C antigen.

14. The pharmaceutical composition according to claim 9, wherein the at least one binding domain is specific for a member of the classical and alternative complement activation cascade selected from the group consisting of C2, C4, C3-convertase, C5, C6, C7, C8 and C9.

15. The pharmaceutical composition according to claim 9, wherein the at least one binding domain is specific for an FcγR selected from the group consisting of FcγRI, FcγRII and FcγRIII.

16. The pharmaceutical composition according to claim 9, wherein the at least one binding domain is specific for a complement pathway protein selected from the group consisting of C1q and C3.

17. The pharmaceutical composition according to claim 9, wherein the at least one binding domain is specific for an integrin selected from the group consisting of β1 integrin, VLA-4, E-selectin, P selectin or L-selectin.

18. The pharmaceutical composition according to claim 9, wherein the at least one binding domain is specific for an interleukin selected from the group consisting of IL-1, IL-2, IL-3, IL-4, IL-5, IL-6, IL-8, IL-12, IL-16, IL-17 and IL-23.

19. The pharmaceutical composition according to claim 9, wherein each binding domain is specific for an antigen independently selected from the group consisting of an integrin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CDCP1, DPCR1, DPCR1, dudulin2, FLJ1120584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, VEGF, an interleukin, a viral antigen, an immunoglobulin, an interferon, tumour necrosis factor-α, tumor necrosis factor-β, a colony stimulating factor, a platelet derived growth factor, a bacterial cell surface antigen, a bacterial toxins, a bioterrorism agent, a snake and spider venom and toxin, OX40, histamine, C1q, opsonin, a member of the classical and alternative complement activation cascades, a FcγR, a complement pathway protein, a CD marker protein (Cluster of Differentiation marker, a serum carrier protein, a circulating immunoglobulin molecule, and CD35/CR1.

20. A polynucleotide encoding a multi-specific antibody molecule according to claim 1.

21. A vector comprising a polynucleotide defined in claim 20.

22. A host cell comprising the polynucleotide of claim 20.

23. A host cell comprising three vectors each vector comprising a polynucleotide encoding a different polypeptide chain of a multi-specific antibody molecule according to claim 1.

24. A process comprising expressing a multi-specific molecule from a host cell defined in claim 22.

* * * * *